US005705316A

United States Patent [19]
Steinmann et al.

[11] Patent Number: 5,705,316
[45] Date of Patent: Jan. 6, 1998

[54] VINYL ETHER COMPOUNDS HAVING ADDITIONAL FUNCTIONAL GROUPS OTHER THAN VINYL ETHER GROUPS AND THE USE THEREOF IN THE FORMULATION OF CURABLE COMPOSITIONS

[75] Inventors: Bettina Steinmann, Praroman; Adrian Schulthess, Tentlingen; Max Hunziker, Düdingen, all of Switzerland

[73] Assignee: Ciba Specialty Chemicals Corporation, Tarrytown, N.Y.

[21] Appl. No.: 555,821

[22] Filed: Nov. 9, 1995

Related U.S. Application Data

[62] Division of Ser. No. 304,464, Sep. 12, 1994, abandoned.

[30] Foreign Application Priority Data

Sep. 16, 1993 [CH] Switzerland ............ 2786/93-3
Mar. 8, 1994 [CH] Switzerland ............ 0684/94-3

[51] Int. Cl.⁶ .......... G03F 7/028; G03C 9/08; C08G 59/18
[52] U.S. Cl. .......... 430/269; 522/90; 522/96; 522/97; 522/100; 522/103; 522/170; 522/181; 522/182; 522/174; 522/179
[58] Field of Search .......... 522/170, 181, 522/182, 100, 90, 96, 97, 179, 174, 103; 430/269

[56] References Cited

U.S. PATENT DOCUMENTS

| | | | |
|---|---|---|---|
| 2,692,256 | 10/1954 | Bauer et al. | 260/86.1 |
| 3,708,296 | 1/1973 | Schlesinger . | |
| 4,098,918 | 7/1978 | De Majistre | 427/36 |
| 4,339,567 | 7/1982 | Green et al. | 528/102 |
| 4,378,277 | 3/1983 | Smith | 204/159.18 |
| 4,383,025 | 5/1983 | Green et al. | 430/280 |
| 4,394,403 | 7/1983 | Smith | 427/42 |
| 4,398,014 | 8/1983 | Green et al. | 528/89 |
| 4,624,912 | 11/1986 | Zweifel et al. | 430/258 |
| 4,751,102 | 6/1988 | Adair et al. | 427/53.1 |
| 4,772,530 | 9/1988 | Gottschalk et al. | 430/138 |
| 4,772,541 | 9/1988 | Gottschalk et al. | 430/339 |
| 4,868,288 | 9/1989 | Meier | 534/15 |
| 4,980,430 | 12/1990 | Liu et al. | 522/100 |
| 5,045,572 | 9/1991 | Plotkin et al. | 522/31 |
| 5,073,476 | 12/1991 | Meier et al. | 430/280 |
| 5,244,985 | 9/1993 | Nobe et al. | 522/170 |
| 5,494,618 | 2/1996 | Sitzmann et al. | 264/401 |
| 5,495,029 | 2/1996 | Steinmann et al. | 549/545 |
| 5,510,226 | 4/1996 | Lapin et al. | 430/269 |

FOREIGN PATENT DOCUMENTS

| | | |
|---|---|---|
| 1300307 | 5/1992 | Canada . |
| 0223587 | 5/1987 | European Pat. Off. . |
| 0429250 | 5/1991 | European Pat. Off. . |
| 2270269 | 12/1975 | France . |
| 1027401 | 4/1958 | Germany . |
| 836046 | 6/1960 | United Kingdom . |
| 1436443 | 5/1976 | United Kingdom . |
| 8903816 | 5/1989 | WIPO . |
| 89/08021 | 9/1989 | WIPO . |
| 9001512 | 2/1990 | WIPO . |
| 90/03989 | 4/1991 | WIPO . |
| 9105814 | 5/1991 | WIPO . |
| 9220014 | 11/1992 | WIPO . |

OTHER PUBLICATIONS

Chem. Abstr. No. 109994c, vol. 80, No. 20, 1974.
Chem. Abstr. No. 164616v, vol. 83, No. 20, 1975.
Chem. Abstr. No. 172546c, vol. 101, No. 20, 1984.
Chem. Abstr. No. 11927a, vol. 121, No. 2, Jan. 1994.
Chem. Abstr. No. 120749u, vol. 120, No. 10, 1994.
Chem. Abstr. No. 113055v, vol. 118, No. 12, 1993.
Chem. Abstr. No. 103626k, vol. 114, No. 12, 1991.
Chem. Abstr. No. 73736x, vol. 115, No. 8, 1991.
Chem. Abstr. No. 73713n, vol. 115, No.. 8, 1991.
Chem. Abstr. No. 114308g, vol. 93, No. 11.
Chem. Abstr. No. 39104v, vol. 68, No. 9.
Chem. Abstr. No. 300219e, vol. 120, No. 24, 1994.
Chem. Abstr. No. 16985f, vol. 93, No. 2.
Tetrahedron Letters, vol. 25, No. 2, pp. 123–126, 1984.
Journal of Polymer Science, Polymer Chemistry Edition, vol. 16, 1367–1373 (1978).
Makromol. Chem., Rapid Commun. 12, 447–453 (1991).
P. Jacobs, Rapid Prototyping & Manufacturing Fundamentals of Stereolithography Soc. of Manuft. Engineers, 1992, p. 256.
R. Storey et al., "New Epoxy–Terminated Oligoesters: Precursors to Totally Biodegradable Networks", Journal of Polymer Science, vol. 31, 1825–1838 (1993).
Crivello et al, Journal Radiation Curing, Jan. 1983, pp. 7–13.

*Primary Examiner*—Susan W. Berman
*Attorney, Agent, or Firm*—David R. Crichton

[57] ABSTRACT

The invention relates to compounds having at least one vinyl ether group which also contain in the molecule at least one further functional group selected from acrylate, methacrylate, epoxy, alkenyl, cycloalkenyl and vinylaryl groups, to compositions, especially for stereolithography, comprising those vinyl ether compounds, and to a method of producing three-dimensional objects using those compositions.

16 Claims, No Drawings

VINYL ETHER COMPOUNDS HAVING ADDITIONAL FUNCTIONAL GROUPS OTHER THAN VINYL ETHER GROUPS AND THE USE THEREOF IN THE FORMULATION OF CURABLE COMPOSITIONS

This is a division of Ser. No. 08/304,464, filed Sep. 12, 1994, now abandoned.

The invention relates to novel vinyl ether compounds, to the use thereof and to compositions comprising those compounds, and also to the use of those compositions in the production of cured products, especially in accordance with the stereolithographic method.

It has long been known to use compounds having carbon-carbon double bonds as a polymerisable constituent of curable compositions, inter alia also polyvinyl ether compounds. In specific cases it may be desirable to carry out the curing of a polymerisable composition in stages. For example, WO 92/20014 describes polymerisable compositions which, in addition to a vinyl ether compound, comprise an epoxy compound as a further polymerisable constituent. Using those compositions it is possible to produce stereolithographically mouldings that are especially faithful to the mould.

Compositions such as those described also have disadvantages, however. For example, they have only relatively little photosensitivity. Furthermore, the mechanical properties, especially the modulus of elasticity (E modulus) and the elongation at tear, of materials obtained using such compositions are often unsatisfactory. The problem underlying the present invention is therefore to obtain further improvements in respect of the said disadvantageous properties of the compositions in question. Surprisingly it has been found that by using vinyl ether compounds as a polymerisable component it is possible to obtain compositions capable of being cured by radiation that are of great sensitivity and that, in addition, produce in the fully cured state a homogeneous material having a high network density and a high modulus of elasticity and also good tear resistance if the vinyl ether compounds contain in the molecule, in addition to the vinyl ether groups, functional groups other than vinyl ether groups that are capable of a cross-linking reaction, such as acrylate, methacrylate, epoxy, alkenyl, especially vinylalkyl, cycloalkenyl and vinylaryl groups, especially styryl groups.

The invention therefore relates to compounds having at least one vinyl ether group which also contain in the molecule at least one further functional group selected from acrylate, methacrylate, epoxy, alkenyl, cycloalkenyl and vinylaryl groups.

The vinyl ether compounds according to the invention preferably have a molecular weight of less than 3000 and are likewise preferably flowable at room temperature, that is to say at approximately from 10° to 30° C.

Preferred examples of the vinyl ether compounds according to the invention are the compounds of the formula $[H_2C=CH-O]_z A$, the symbols used in that formula and in the formulae below having the following definitions:

A is a z-valent radical selected from the radicals of the following formulae (1), (2), (3) and (4)

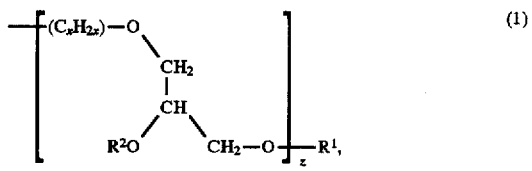 (1)

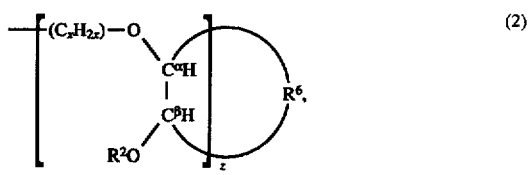 (2)

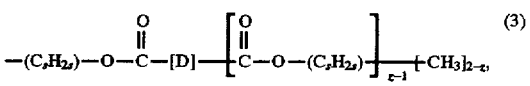 (3)

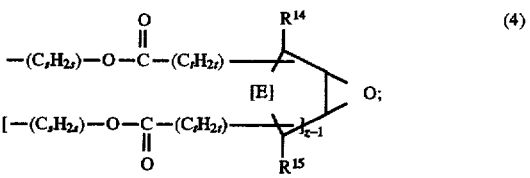 (4)

[D] is a group of the formula

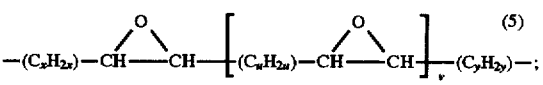 (5)

[E] is a $C_1$- or a $C_2$-alkylene group;

$R^0$ is a hydrogen atom or a methyl group;

$R^1$ is a z-valent radical selected from aliphatic, cycloaliphatic, aromatic, aliphatic-aromatic and aliphatic-cycloaliphatic radicals and polyoxyalkylene radicals;

$R^2$ is a radical selected from the radicals of the formulae

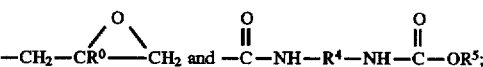

$R^4$ is a group selected from the groups of the formulae

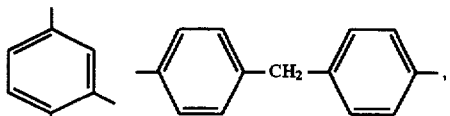

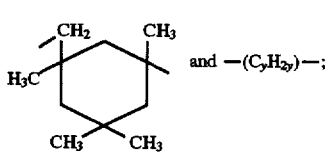 and $-(C_yH_{2y})-$;

$R^5$ is a group selected from the groups of the formulae

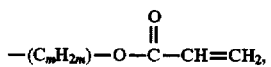

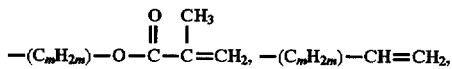

-continued

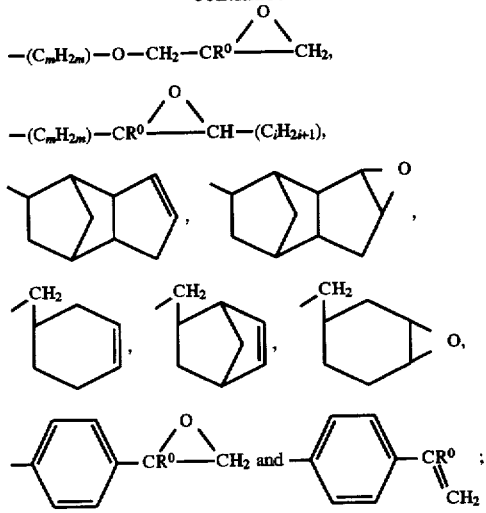

$R^6$ is a (2.z)-valent organic group which, together with the carbon atoms $C^{60}$ and $C^{62}$ of each of the z groups of the formula

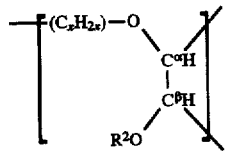    (6)

in a radical of formula (2), forms a cycloaliphatic ring having at least 5 carbon atoms;

$R^{14}$ and $R^{15}$ are each a hydrogen atom or, when [E] is a $C_2$ alkylene group, are each a hydrogen atom or together form a methylene group;

i is an integer from 0 to 20;

m is an integer from 1 to 20;

s is an integer from 2 to 10;

t is an integer from 0 to 10;

u in the individual units of the formula

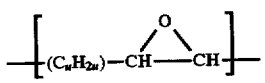

are independently of one another an integer from 1 to 20;

v is an integer from 0 to 4;

x and y are independently of one another an integer from 2 to 20, and z is the number 1 or 2.

The compounds according to the invention wherein A is a radical of formula (1) or (2) preferably have one of the formulae

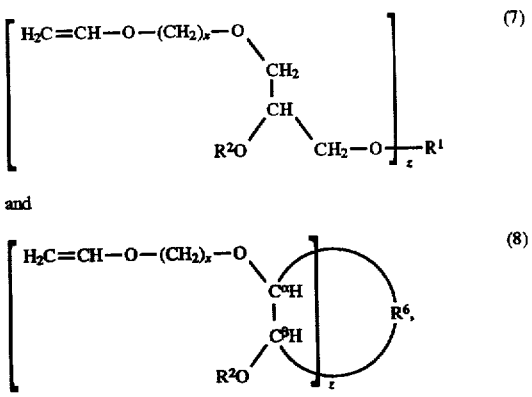

and (8)

wherein $R^1$, $R^2$, $R^6$, x, z and the other symbols are as defined above.

The indices i, m, s, t, u, x and y advantageously have an upper limit of 8, and the indices i, m, s, t and u especially advantageously have an upper limit of 6 or 4.

$R^0$ is preferably a hydrogen atom and $R^2$ is preferably

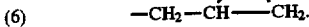

In the compounds according to the invention $R^1$ is preferably a z-valent radical selected from
   a) aliphatic radicals having from 2 to 20 carbon atoms,
   b) cycloaliphatic and aromatic radicals each having from 6 to 14 carbon atoms,
   c) aliphatic-aromatic and aliphatic-cycloaliphatic radicals each having from 7 to 25 carbon atoms, and
   d) polyoxyalkylene radicals of the formulae $R^7$—$[OC_gH_{2g}]_n$— and —$(C_gH_{2g})$—$[OC_gH_{2g}]_{n-1}$ —wherein
      $R^7$ is an alkyl group having from 1 to 8 carbon atoms,
      g is a number from 1 to 8 in accordance with the average number of carbon atoms of an alkylene unit of the polyoxyalkylene radical and
      n is an integer from 2 to 20.

The symbol "g" indicates the number of carbon atoms calculated as being the average for an alkylene unit in the corresponding polyoxyalkylene group. The index g need not, therefore, be a whole number, since the polyoxyalkylene group may have been formed from monomers having different numbers of carbon atoms which, in addition, may have been used in different proportions. Examples of possible monomers are ethylene oxide, propylene oxide and tetrahydrofuran. The index g preferably has the value 2 or 3 or a value between 2 and 3, and is therefore a polyether composed of ethylene oxide and/or propylene oxide units.

$R^1$ may be unsubstituted or in addition may have one or more substituents which in the case of an aliphatic radical $R^1$ are selected from $C_1$–$C_4$alkoxy and halogen substituents; and in the case of other types of radical $R^1$ are selected from $C_1$–$C_4$alkyl, $C_1$–$C_4$alkoxy and halogen substituents.

$R^1$ is especially a radical selected from the radicals of the formulae $(C_fH_{2f+1})-$, $-(C_fH_{2f})-$, $CH_3-[O-\underset{\underset{R^3}{|}}{CH}-CH_2]_n-$, $-(\underset{\underset{R^3}{|}}{CH}-CH_2)-[O-\underset{\underset{R^3}{|}}{CH}-CH_2]_{n-1}-$,

[structure: two phenyl groups connected by C bearing R and R³]

[structure: two cyclohexyl groups connected by C bearing R and R³]

and phenyl; wherein

R and
R³ are independently of one another a hydrogen atom or methyl and
f is an integer from 2 to 20.
n has again the definition already given above of an integer from 2 to 20, preferably from 2 to 10.

Finally, special preference is given to the compounds of formula (7) wherein R¹ is a radical selected from the radicals of the formulae $-(C_fH_{2f})-$, $-(\underset{\underset{R^3}{|}}{CH}-CH_2)-[O-\underset{\underset{R^3}{|}}{CH}-CH_2]_{n-1}-$,

[structure: two phenyl groups connected by C bearing R and R³]

and phenyl

R⁴ is a group selected from the groups of the formulae

[structure: dimethylphenyl group], [structure: trimethylcyclohexyl / isophorone-type group with H₃C, CH₂, CH₃, CH₃, CH₃]

and $-(C_yH_{2y})-$, for example $-(CH_2)_6-$;

R⁵ is a group selected from the groups of the formulae $-(C_kH_{2k})-O-\overset{\overset{O}{\|}}{C}-CH=CH_2$, $-(C_2H_{2k})-O-\overset{\overset{O}{\|}}{C}-\underset{\underset{CH_3}{|}}{C}=CH_2$ $-(C_mH_{2m})-CH=CH_2$, [cyclohexenyl structure with CH₂] and

[dicyclopentadienyl-type bicyclic structure];

and
R and
R³ are both either a hydrogen atom or methyl; and
k is an integer from 2 to 10, and the index m has an upper limit of 10, and the comments made above apply to the remaining symbols.

Examples of such compounds are those in which

R¹ is a radical selected from an alkylene radical having from 2 to 4 carbon atoms, a phenyl radical and a radical of the formula

[structure: two phenyl groups connected by C bearing R and R³],

R⁴ is a group of the formula

[structure: dimethylphenyl group with CH₃]

and

R⁵ is a group selected from the groups of the formulae $-(C_2H_4)-O-\overset{\overset{O}{\|}}{C}-CH=CH_2$, $-(C_2H_4)-O-\overset{\overset{O}{\|}}{C}-\underset{\underset{CH_3}{|}}{C}=CH_2$, $-CH_3-CH=CH_2$ and [dicyclopentadienyl-type bicyclic structure].

The vinyl ether compounds wherein A is a radical of formula (1), that is to say, for example, the compounds of formula (7), can be prepared, for example, by first reacting the glycidyl ether $R^1[O-CH_2-\overset{\overset{O}{\diagup \diagdown}}{CH-\!\!-\!\!-\!\!-CH_2}]_k$ with a hydroxyalkylvinyl ether of the formula $H_2C=CH-O-(C_xH_{2x})-OH$ to form a compound of the formula $\left[ H_2C=CH-O-(C_xH_{2x})-O.CH_2-\underset{\underset{OH}{|}}{CH}-CH_2-O \right]_k\!\!\!-R^1$ and either converting the hydroxy group into a glycidyl ether group or allowing the hydroxy group to react further with the diisocyanate of the formula OCN—R⁴—NCO and the hydroxy compound R⁵OH or with an adduct of those two reactants.

The compounds wherein A is a radical of formula (2), for example the compounds of formula (8), have at least one cycloalkyl radical that is formed by the two carbon atoms C^α and C^β of a structural unit of the formula $H_2=CH-O-\left[-(C_xH_{2x})-O\diagdown\!\!\atop{C^\alpha H\atop |\atop C^\beta H}\diagup\atop R^2O\right]$ (9)

and the entire radical R⁶ or by the two carbon atoms C^α and C⁶² of a structural unit of formula (9) and parts of the radical R⁶. The term "cycloalkyl group" is to be understood as including especially also polycycloalkyl radicals, for example bicycloalkyl radicals. The term is also intended to include cycloalkyl groups consisting of two spiro-linked rings.

Preferably $R^6$ is an organic group having from 3 to 50, especially from 3 to 30 and more especially from 3 to 20, carbon atoms and $R^2$ is a radical selected from the radicals of the formulae

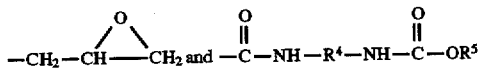

wherein $R^4$ is a group selected from the groups of the formulae

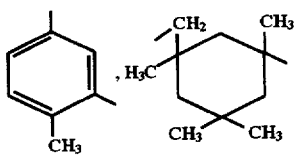

and $-(C_yH_{2y})-$, for example $-(CH_2)_6-$, and $R^5$ is a group selected from the groups of the formulae

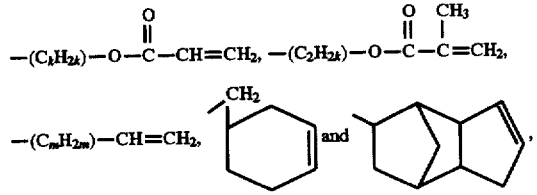

k is an integer from 2 to 10, and
m is an integer from 1 to 10.

The compounds according to the invention wherein A is a group of formula (2) comprise, for example, compounds in which $R^6$ together with the carbon atoms $C^\alpha$ and $C^{62}$ of the group of formula (9) forms a cycloalkyl radical having from 5 to 7 ring carbon atoms, especially a cyclopentyl or cyclohexyl radical, and z is 1.

The compounds according to the invention wherein A is a group of formula (2) also comprise compounds of a structural type in which $R^6$ is a group of the formula $R^8-[G]-R^9$ wherein
$R^8$ together with the carbon atoms $C^\alpha$ and $C^\beta$ of a group of formula (9) already mentioned above forms a cycloalkyl radical having from 5 to 7 ring carbon atoms, especially a cyclopentyl or cyclohexyl ring, to which a further cycloalkyl radical having from 5 to 7 ring carbon atoms may have been fused; and $R^9$ either likewise forms, together with the carbon atoms $C^\alpha$ and $C^\beta$ of a further group of formula (9), a cycloalkyl radical having from 5 to 7 ring carbon atoms, especially a cyclopentyl or cyclohexyl ring, to which a further cycloalkyl radical having from 5 to 7 ring carbon atoms may have been fused, or is itself a cycloalkyl radical having from 5 to 7 ring carbon atoms, especially a cyclopentyl or cyclohexyl ring, to which a further cycloalkyl radical having from 5 to 7 ring carbon atoms may have been fused.

[G] in the above formula is a structural unit selected from a single bond and the groups of the formulae

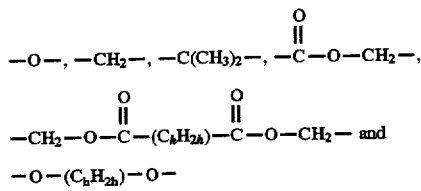

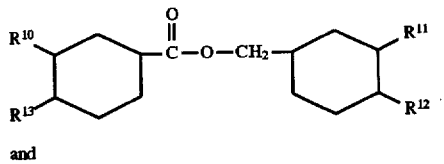

and
h is an integer from 1 to 6, especially from 2 to 4.
Specific examples of the last-mentioned compounds are the compounds of the formulae

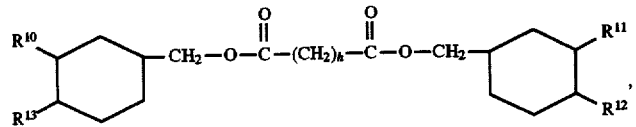

and

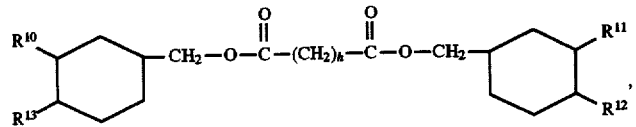

wherein one of the radicals $R^{10}$ and $R^{13}$ is a group of the formula $H_2C=CH-O-(CH_2)_x-O-$ and the other is a group of the formula $R^2O-$ and, likewise, one of the radicals $R^{11}$ and $R^{12}$ is a group of the formula $H_2C=CH-O-(CH_2)_x-O-$ and the other is a group of the formula $R^2O-$, wherein x and h are each independently of the other an integer from 2 to 4.

The vinyl ether compounds wherein A is a group of formula (2) can be prepared, for example, analogously to the process described above for the preparation of vinyl ether compounds of formula (1) from cycloaliphatic epoxy compounds having the general structural formula

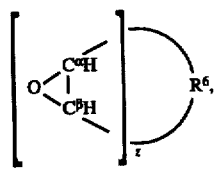

wherein $R^6$ corresponds to an organic group as already defined above, by reacting those compounds with a suitable hydroxyalkylvinyl ether and either converting the free hydroxy group formed in that reaction in customary manner into a glycidyl ether group or reacting the hydroxy group with the desired diisocyanate $R^4(NCO)_2$ and the alcohol $R^5OH$. Typical examples of suitable cycloaliphatic epoxy compounds are:
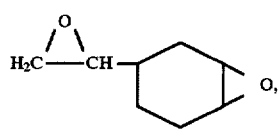
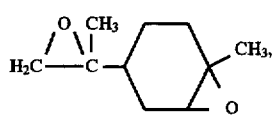
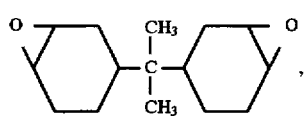
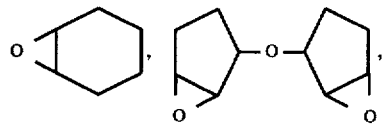
especially the liquid isomer thereof,
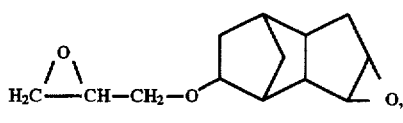
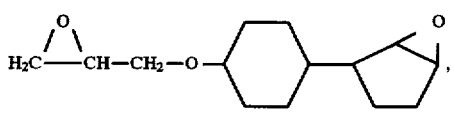
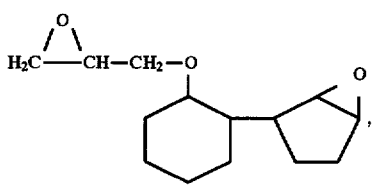
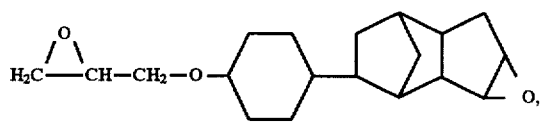
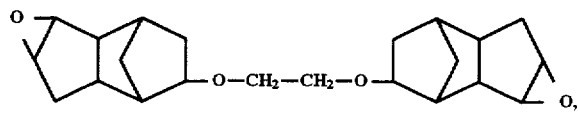
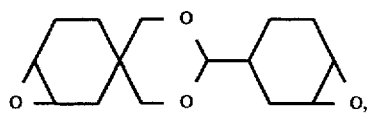
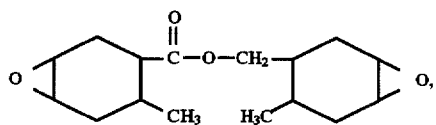
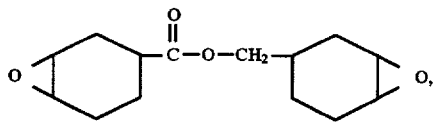
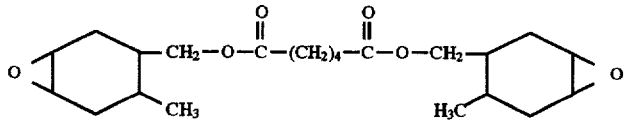
and -continued

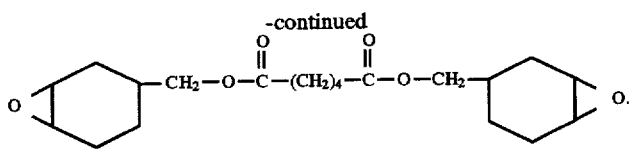

Of the compounds of formula [H₂C=CH—O—]ₛA wherein A is a radical of formula (3) or (4), preferred compounds are generally those wherein the index s is an integer from 2 to 4, preferably 2 or 4, t is an integer from 0 to 2, u is the number 1, v is the number 0 or 1, and x and y are each an integer from 2 to 10.

Special emphasis should be given to those compounds of the mentioned type having the formula

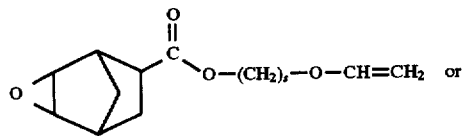

or

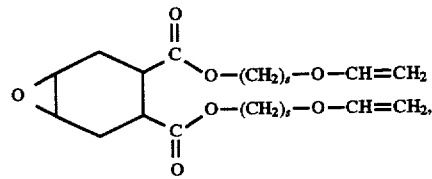

wherein s is an integer from 2 to 10, especially 2 or 4.

In a further preferred form of those vinyl ether compounds wherein

A is a radical of formula (4)

R¹⁴ and

R¹⁵ are both a hydrogen atom and z is 1.

Preparation processes for the mentioned compounds are known to the person skilled in the art.

For example, compounds of the formula [H₂C=CH—O—]ₛA wherein A is a radical of formula (3) can be prepared, for example, starting from carboxylic acids of the formula HOOC—[D¹]—CH₃ or HOOC—[D¹]—COOH wherein [D¹] is a radical of the formula —(C$_x$H$_{2x}$)—CH=CH—[—(C$_u$H$_{2u}$)—CH=CH—]$_v$—(C$_y$H$_{2y}$)— and u, v, x and y are likewise as already defined above, or starting from corresponding fatty acid esters, for example corresponding methyl esters, by first oxidising those acids or esters at the double bonds in known manner with peracids prepared in situ and thus convening them into the corresponding epoxy compounds which are then reacted with the desired hydroxyalkylvinyl ether of the formula H₂C=CH—O—(C$_r$H$_{2r}$)—OH to form the end product of the formula H₂C=CH—O—(C$_r$H$_{2r}$)—OOC—[D]—CH₃ or of the formula H₂C=CH—O—(C$_r$H$_{2r}$)—OOC—[D]—COO—(C$_r$H$_{2r}$)—O—CH=CH₂.

Analogously, for the preparation of vinyl ether compounds of formula

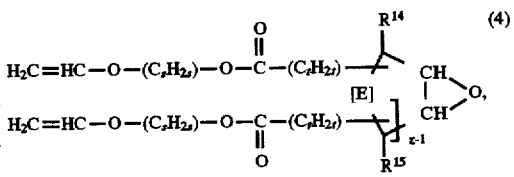

the starting materials used can be compounds of the formula

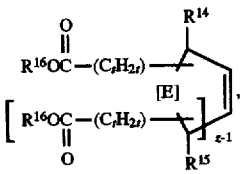

wherein R¹⁶ is a hydrogen atom or an alkyl group, for example a methyl group, and the remaining symbols are as already defined above, which compounds can be reacted in accordance with an analogous epoxidisation reaction likewise with the desired vinyl ethers of the formula H₂C=CH—O—(C$_r$H$_{2r}$)—OH.

The vinyl ether compounds according to the invention represent a valuable formulation component for compositions curable by radiation. The invention therefore relates also to the use thereof as a polymerisable component of such compositions.

Such compositions also comprise one or more of the photoinitiators described hereinbelow in an effective amount, for example from 0.5 to 20% by weight, based on the total weight of the composition.

Preference is given to compositions which, in addition to one or more of the vinyl ether compounds according to the invention and one or more photoinitiators, also comprise at least one polymerisable compound other than the vinyl ether compounds according to the invention.

Additional polymerisable compounds that may be used are, for example, customary radically polymerisable compounds, generally in amounts of from 0 to 80% by weight, based on the total composition, such as monoacrylates, di- and poly-acrylates having an acrylate functionality of up to 9 or corresponding methacrylates and also vinyl compounds having a vinyl functionality of up to 6.

Suitable mono(meth)acrylates are, for example, allyl acrylate, allyl methacrylate, methyl, ethyl, n-propyl, n-butyl, isobutyl, n-hexyl, 2-ethylhexyl, n-octyl, n-decyl and n-dodecyl acrylate and methacrylate, 2-hydroxyethyl, 2- and 3-hydroxypropyl acrylate and methacrylate, 2-methoxyethyl, 2-ethoxyethyl and 2- or 3-ethoxypropyl acrylate, tetrahydrofurfuryl methacrylate, 2-(2-ethoxyethoxy)ethyl acrylate, cyclohexyl methacrylate, 2-phenoxyethyl acrylate, glycidyl acrylate and isodecyl acrylate, and a suitable mono-N-vinyl compound is N-vinylpyrrolidone or N-vinylcaprolactam. Such products are likewise known and some of them are commercially available, for example from the SARTOMER Company.

Additional suitable di(meth)acrylates are, for example, the di(meth)acrylates of cycloaliphatic or aromatic diols, such as 1,4-dihydroxymethylcyclohexane, 2,2-bis(4-hydroxy-cyclohexyl)propane, bis(4-hydroxycyclohexyl)methane, hydroquinone, 4,4'-dihydroxybiphenyl, bisphenol A, bisphenol F, bisphenol S, ethoxylated or propoxylated bisphenol A, ethoxylated or propoxylated bisphenol F or ethoxylated or propoxylated bisphenol S. Such di(meth)acrylates are known and some of them are commercially available.

It is also possible to use as di(meth)acrylates compounds of formulae (4), (5), (6) and (7)

by reacting ethoxylated bisphenols, especially ethoxylated bisphenol A, or diglycidyl ethers of bisphenol, especially the diglycidyl ether of bisphenol A, with (meth)acrylic acid to form the compounds of formulae (4) and (5).

In the same way it is also possible to prepare the compounds of formulae (6) and (7) by reacting a diglycidyl ether of formula (6a)

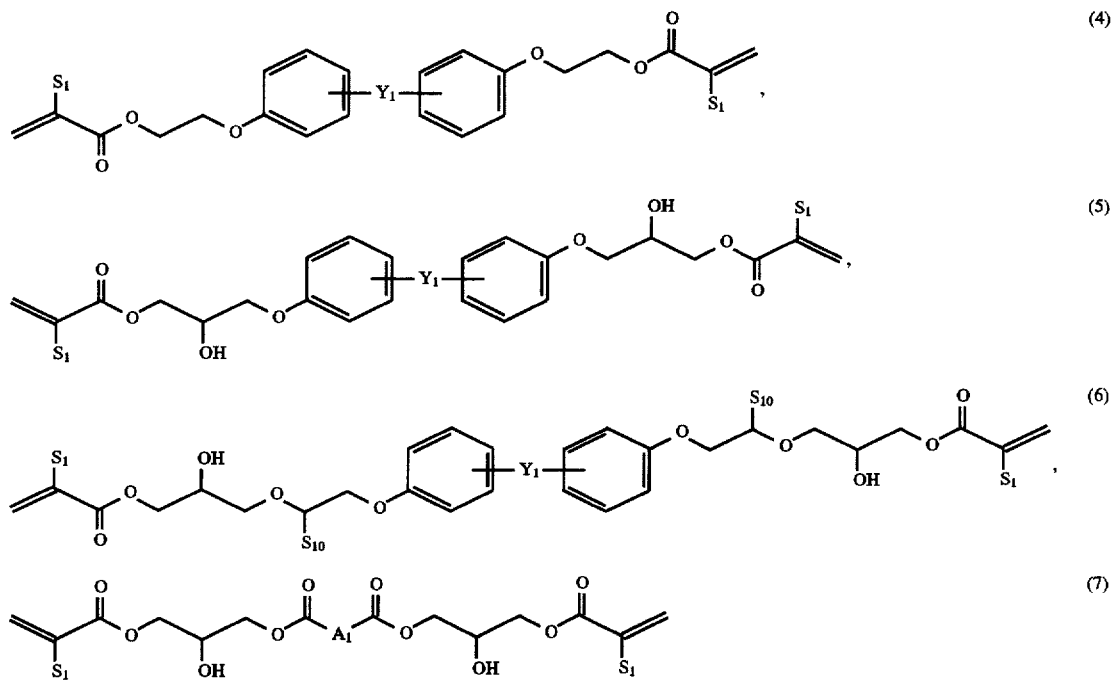

wherein
$S_1$ is a hydrogen atom or methyl,
$Y_1$ is a direct bond, $C_1$–$C_6$ alkylene, —S—, —O—, —SO—, —SO$_2$— or —CO—,
$S_{10}$ is a $C_1$–$C_8$ alkyl group, a phenyl group that is unsubstituted or substituted by one or more $C_1$–$C_4$alkyl

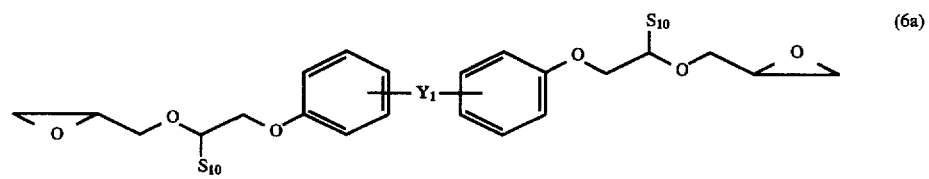

groups, hydroxy groups or halogen atoms, or is a radical of the formula —CH$_2$—OS$_{11}$ wherein
$S_{11}$ is a $C_1$–$C_8$alkyl group or a phenyl group and
$A_1$ is a radical selected from the radicals of the formulae

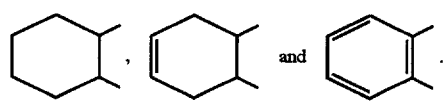

The di(meth)acrylates of formulae (4) and (5) are known and some are commercially available, for example under the names SR® 349 or Novacure® 3700, and can be prepared or a diglycidyl ester of formula (7a)

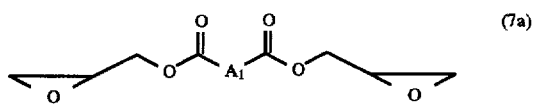

with (meth)acrylic acid to form the compounds of formulae (6) and (7) wherein $S_{10}$, $Y_1$ and $A_1$ are as defined above.

It is also possible to use as diacrylates compounds of formulae (8), (9), (10) and (11)

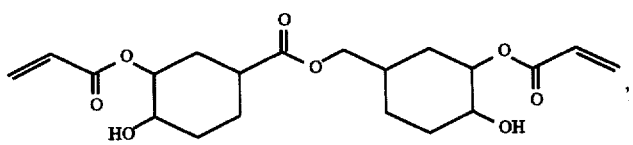

(8)

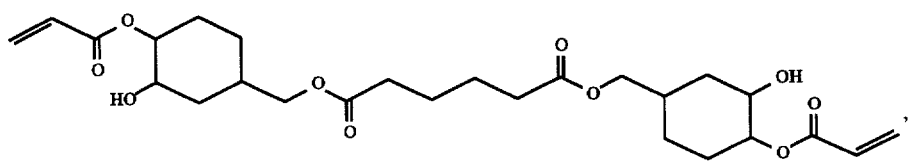

(9)

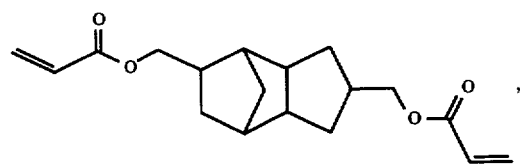

(10)

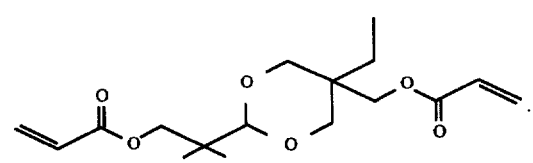

(11)

Those compounds are known and some of them are commercially available. For example, the compounds of formulae (8) and (9) can be obtained in known manner by reacting the cycloaliphatic diepoxides of formulae (8a) and (9a)

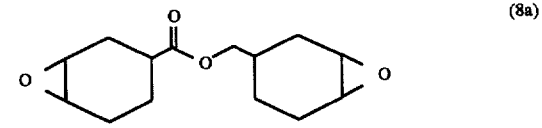

(8a)

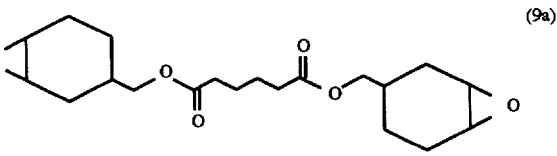

(9a)

with (meth)acrylic acid to form the compounds of formulae (8) and (9), respectively. The compound of formula (11) is commercially available under the name Kayatari® R-604.

Additional suitable poly(meth)acrylates are, for example, monomeric or oligomeric aliphatic, cycloaliphatic or aromatic acrylates or methacrylates having a (meth)acrylate functionality greater than 2, especially tri-, tetra- or pentafunctional acrylates or methacrylates.

Suitable aliphatic polyfunctional (meth)acrylates are, for example, the triacrylates and trimethacrylates of hexane-2,4,6-triol, glycerol or 1,1,1-trimethylolpropane, ethoxylated or propoxylated glycerol or 1,1,1-trimethylolpropane and the hydroxy-group-containing tri(meth)acrylates which can be obtained by reaction of triepoxy compounds, for example the triglycidyl ethers of the mentioned triols, with (meth) acrylic acid. It is also possible to use, for example, pentaerythritol tetraacrylate, bistrimethylolpropane tetraacrylate, pentaerythritol monohydroxy-triacrylate or -trimethacrylate or dipentaerythritol monohydroxypentaacrylate or -pentamethacrylate.

In addition, further compounds polymerisable by radiation that can be used in the compositions according to the invention are hexafunctional or higher-functional urethane acrylates or urethane methacrylates. Those urethane (meth) acrylates are known to the person skilled in the art and can be prepared in known manner, for example by reacting a hydroxy-terminated polyurethane with acrylic acid or methacrylic acid, or by reacting an isocyanate-terminated prepolymer with hydroxyalkyl (meth)acrylates to form the urethane (meth)acrylate.

Suitable aromatic tri(meth)acrylates are, for example, the reaction products with (meth)acrylic acid of triglycidyl ethers of trivalent phenols and phenol- or cresol-novolaks having three hydroxy groups.

The compositions according to the invention preferably comprise at least one liquid (meth)acrylate having an acrylate functionality of from 1 to 9, and comprise especially a liquid mixture of aromatic, aliphatic or cycloaliphatic (meth) acrylates having an acrylate functionality of from 1 to 9.

Furthermore, the compositions according to the invention may comprise as additional polymerisable components cationically polymerisable organic material, generally likewise in amounts of from 0 to 80% by weight, based on the total composition. Such additional components are especially epoxy compounds, preferably those which are flowable at temperatures of approximately from 10° to 30° C. The epoxy resins used in the compositions according to the invention are generally compounds having on average more than one 1,2-epoxy group in the molecule.

Such resins may have an aliphatic, aromatic, cycloaliphatic, araliphatic or heterocyclic structure; they contain epoxy groups as side groups, or those groups form part of an alicyclic or heterocyclic ting system. Such epoxy resins are generally known and commercially available.

The following may be mentioned as examples of such epoxy resins:

I) Polyglycidyl and poly(β-methylglycidyl) esters obtainable by reaction of a compound having at least two carboxy groups in the molecule and epichlorohydrin or glycerol dichlorohydrin or β-methyl-epichlorohydrin. The reaction is advantageously carried out in the presence of bases.

As compounds having at least two carboxy groups in the molecule there may be used aliphatic polycarboxylic acids. Examples of such polycarboxylic acids are glutaric acid, adipic acid, pimelic acid, suberic acid, azelaic acid, sebacic acid and dimerised or trimerised linoleic acid.

It is also possible, however, to use cycloaliphatic polycarboxylic acids, for example tetrahydrophthalic acid, 4-methyltetrahydrophthalic acid, hexahydrophthalic acid or 4-methylhexahydrophthalic acid.

It is also possible to use aromatic polycarboxylic acids, for example phthalic acid, isophthalic acid, trimellitic acid or pyromellitic acid.

Carboxy-terminated adducts, for example of trimellitic acid and polyols, for example glycerol or 2,2-bis(4-hydroxycyclohexyl)propane, may also be used.

II) Polyglycidyl or poly(β-methylglycidyl) ethers obtainable by reaction of a compound having at least two free alcoholic hydroxy groups and/or phenolic hydroxy groups and a suitably substituted epichlorohydrin under alkaline conditions, or in the presence of an acid catalyst and subsequent treatment with alkali.

Ethers of that type are derived, for example, from acyclic alcohols, such as ethylene glycol, diethylene glycol and higher poly(oxyethylene) glycols, propane-1,2-diol, or poly (oxypropylene) glycols, propane-1,3-diol, butane-1,4-diol, poly(oxytetramethylene) glycols, pentane-1,5-diol, hexane-1,6-diol, hexane-2,4,6-triol, glycerol, 1,1,1-trimethylolpropane, bistrimethylolpropane, pentaerythritol, sorbitol, and also from polyepichlorohydrins.

However, they are also derived, for example, from cycloaliphatic alcohols, such as 1,3- or 1,4-dihydroxycyclohexane, bis(4-hydroxycyclohexyl)methane, 2,2-bis(4-hydroxycyclohexyl)propane or 1,1-bis(hydroxymethyl)cyclohex-3-ene, or they have aromatic nucleii, such as N,N-bis(2-hydroxyethyl)aniline or p,p'-bis(2-hydroxyethylamino)-diphenylmethane.

The epoxy compounds can also be derived from mononuclear phenols, for example from resorcinol or hydroquinone, or they are based on polynuclear phenols, for example on bis(4-hydroxyphenyl)methane (bisphenol F), 2,2-bis(4-hydroxyphenyl)propane (bisphenol A), or on condensation products, obtained under acid conditions, of phenols or cresols with formaldehyde, such as phenol-novolaks and cresol-novolaks.

III) Poly(N-glycidyl) compounds are obtainable, for example, by dehydrochlorination of the reaction products of epichlorohydrin with amines that contain at least two amine hydrogen atoms. Such amines are, for example, n-butylamine, aniline, toluidine, m-xylylenediamine, bis(4-aminophenyl)methane or bis(4-methylaminophenyl) methane.

The poly(N-glycidyl) compounds also include, however, N,N'-diglycidyl derivatives of cycloalkyleneureas, such as ethyleneurea or 1,3-propyleneurea, and N,N'-diglycidyl derivatives of hydantoins, such as 5,5-dimethylhydantoin.

IV) Examples of poly(S-glycidyl) compounds are di-S-glycidyl derivatives derived from dithiols, for example ethane-1,2-dithiol or bis(4-mercaptomethylphenyl) ether.

V) Examples of epoxy compounds wherein the epoxy groups form part of an alicyclic or heterocyclic ring system are, for example, bis(2,3-epoxycyclopentyl) ether, 2,3-epoxycyclopentylglycidyl ether, 1,2-bis(2,3-epoxycyclopentyloxy)ethane, bis(4-hydroxycyclohexyl) methanediglycidyl ether, 2,2-bis(4-hydroxycyclohexyl) propanediglycidyl ether, 3,4-epoxycyclohexylmethyl-3,4-epoxycyclohexanecarboxylate, 3,4-epoxy-6-methylcyclohexylmethyl-3,4-epoxy-6-methylcyclohexanecarboxylate, di(3,4-epoxycyclohexylo methyl)hexanedioate, di(3,4-epoxy-6-methyl-cyclohexylmethyl)hexanedioate, ethylene bis(3,4-epoxycyclohexanecarboxylate), ethanediol di(3,4-epoxycyclohexylmethyl) ether, vinylcyclohexene dioxide, dicyclopentadiene diepoxide or 2—(3,4-epoxycyclohexyl-5,5-spiro-3,4-epoxy)cyclohexane-1,3-dioxane.

It is also possible, however, to use epoxy resins in which the 1,2-epoxy groups are bonded to different hetero atoms or functional groups. Those compounds include, for example, the N,N,O-triglycidyl derivative of 4-aminophenol, the glycidyl ether glycidyl ester of salicylic acid, N-glycidyl-N'-(2-glycidyloxypropyl)-5,5-dimethylhydantoin or 2-glycidyloxy-1,3-bis(5,5-dimethyl-1-glycidylhydantoin-3-yl)propane.

Also suitable are liquid prereacted adducts of such epoxy resins with hardeners for epoxy resins.

It is, of course, also possible to use mixtures of epoxy resins in the compositions according to the invention.

The photoinitiators used may be, irrespective of the polymerisable groups present in the components of the compositions according to the invention, both radical photoinitiators and photoinitiators for cationic polymerisation and also mixtures of one or more of the said initiators.

Radical photoinitiators are used especially when compounds having carbon-carbon double bonds are present in the compositions according to the invention, especially when compounds having acrylate, methacrylate and vinyl groups are present. In general it is possible to use any type of photoinitiator that forms free radicals under the appropriate irradiation. Typical compounds of known photoinitiators are benzoins, such as benzoin, benzoin ethers, such as benzoin methyl ether, benzoin ethyl ether and benzoin isopropyl ether, benzoin phenyl ether and benzoin acetate, acetophenones, such as acetophenone, 2,2-dimethoxyacetophenone and 1,1-dichloroacetophenone, benzil, benzil ketals, such as benzil dimethyl ketal and benzil diethyl ketal, anthraquinones, such as 2-methylanthraquinone, 2-ethylanthraquinone, 2-tert-butylanthraquinone, 1-chloroanthraquinone and 2-amylanthraquinone, and also triphenylphosphine, benzoylphosphine oxides, for example 2,4,6-trimethylbenzoyldiphenylphosphine oxide (Luzirin TPO), benzophenones, such as benzophenone and 4,4'-bis(N,N'-dimethylamino)benzophenone, thioxanthones and xanthones, acridine derivatives, phenazine derivatives, quinoxaline derivatives or 1-phenyl-1,2-propanedione-2-O-benzoyloxime, 1-aminophenyl ketones or 1-hydroxyphenyl ketones, such as 1-hydroxycyclohexylphenyl ketone, phenyl (1-hydroxyisopropyl) ketone and 4-isopropylphenyl(1-hydroxyisopropyl) ketone, all of which are known compounds.

Especially suitable photoinitiators, which are usually used in combination with a He/Cd laser as light source, are acetophenones, such as 2,2-dialkoxybenzophenones and 1-hydroxyphenyl ketones, for example 1-hydroxycyclohexylphenyl ketone or 2-hydroxyisopropylphenyl ketone (=2-hydroxy-2,2-dimethylacetophenone), but especially 1-hydroxycyclohexylphenyl ketone.

Another class of radical photoinitiators, which is usually used when argon ion lasers are employed, are the benzil ketals, for example benzil dimethyl ketal. The photoinitiator used is especially an α-hydroxyphenyl ketone, benzil dimethyl ketal or 2,4,6-trimethylbenzoyldiphenylphosphine oxide.

A further class of suitable radical photoinitiators comprises the ionic dye-counter ion compounds which are capable of absorbing actinic rays and generating free radicals which initiate the polymerisation of substances such as (meth)acrylates or vinyl compounds. The mixtures according to the invention that comprise ionic dye-counter ion compounds can in this way be cured in a more controllable way using visible light in an adjustable wavelength range of 400–700 nm. Ionic dye-counter ion compounds and their mode of action are known, for example from EP-A-O 223 587 and U.S. Pat. Nos. 4,751,102; 4,772,530 and 4,772,541. Examples of suitable ionic dye-counter ion compounds that may be mentioned are the anionic dye-iodonium ion complexes, the anionic dye-pyrylium ion complexes and especially the cationic dye-borate anion compounds of the formula

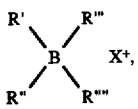

wherein X⁺ is a cationic dye and R', R", R'" and R"" are each independently of the others an alkyl, aryl, alkaryl, allyl, aralkyl, alkenyl or alkynyl group, an alicyclic group or a saturated or unsaturated heterocyclic group.

As photoinitiators for components having cationically polymerisable groups, especially epoxy or vinyl ether groups, there may be used virtually any compounds known for that purpose in the art. Such compounds include, for example, onium salts with anions having weak nucleophilicity. Examples thereof are halonium salts, iodosyl salts or sulfonium salts, as described in EP-A 153 904, sulfoxonium salts, for example as described in EP-A 35 969, 44 274, 54 509 and 164 314, or diazonium salts, for example as described in U.S. Pat. No. 3,708,296. Other cationic photoinitiators are metallocene salts, for example as described in EP-A 94 914 and 94 915.

An overview of further customary onium salt initiators and/or metallocene salts can be found in "UV-Curing, Science and Technology", (Editor: S. P. Pappas, Technology Marketing Corp., 642 Westover Road, Stanford, Conn. USA) or "Chemistry & Technology of UV & EB Formulation for Coatings, Inks & Paints", Vol. 3 (edited by P. K. T. Oldring).

Preferred photoinitiators for cationically polymerisable groups are compounds of formulae (12), (13) and (14)

$$[G_1-I-G_2]^{\oplus}[LQ_w]^{\ominus}, \quad (12)$$

$$\left[\begin{array}{c} O \\ \| \\ G_3-I-G_4 \end{array}\right]^{\oplus} [LQ_w]^{\ominus}, \quad (13)$$

$$\left[\begin{array}{c} G_5 \\ \diagdown \\ S-G_7 \\ \diagup \\ G_6 \end{array}\right]^{\oplus} [LQ_w]^{\ominus}, \quad (14)$$

wherein $G_1$, $G_2$, $G_3$, $G_4$, $G_5$, $G_6$ and $G_7$ are each independently of the others $C_6$–$C_{18}$aryl that is unsubstituted or substituted by suitable radicals, L is boron, phosphorus, arsenic or antimony, Q is a halogen atom, or some of the radicals Q in an anion $LQ_w^-$ may also be hydroxy groups, and w is an integer corresponding to the valency of L+1.

Examples of $C_6$–$C_{18}$aryl are phenyl, naphthyl, anthryl and phenanthryl. Substituents which may be present in suitable radicals are alkyl, preferably $C_6$–$C_6$alkyl, such as methyl, ethyl, n-propyl, isopropyl, n-butyl, sec-butyl, isobutyl, ten-butyl and the various pentyl or hexyl isomers, alkoxy, preferably $C_6$–$C_6$ alkoxy, such as methoxy, ethoxy, propoxy, butoxy, pentyloxy and hexyloxy, alkylthio, preferably $C_6$–$C_6$ alkylthio, such as methylthio, ethylthio, propylthio, butylthio, pentylthio and hexylthio, halogen, such as fluorine, chlorine, bromine and iodine, amino groups, cyano groups, nitro groups, and arylthio, such as phenylthio.

Examples of preferred halogen atoms Q are chlorine and especially fluorine. Preferred anions $LQ_m^-$ are $BF_4^-$, $PF_6^-$, $AsF_6^-$, $SbF_6^-$ and $SbF_5(OH)^-$. $CF_3SO_3^-$ is a preferred cation.

Of course, compounds that contain two or more of the onium groups in the molecule, for example disulfonium compounds, are also suitable as initiators.

Special preference is given to cationic photoinitiators of formula (14) wherein $G_5$, $G_6$ and $G_7$ are phenyl or biphenyl, or mixtures of those two compounds.

A further preferred type of cationic photoinitiators has the formula (15)

$$[g_a(Fe^{II}G_9)_c]_d^{+e}[T]_c^{-d} \quad (15),$$

wherein

C is 1 or 2, d is 1,2,3,4 or 5,

T is a non-nucleophilic anion, for example $BF_4^-$, $PF_6^-$, $AsF_6^-$, $SbF_6^-$, $CF_3SO_3^-$, $C_2F_5SO_3^-$, n-$C_3F_7SO_3^-$, n-$C_4F_9SO_3^-$, n-$C_6F_{13}SO_3^-$, n-$C_8F_{17}SO_3^-$, $C_6F_5SO_3^-$, phosphorus tungstate, $(PO_{40}W_{12}^{3-})$ or silicon tungstate $(SiO_{40}W_{12}^{4-})$, $G_8$ is a π-arene, and $G_9$ is an anion of a π-arene, especially a cyclopentadienyl anion.

Examples of π-arenes as $G_8$ and anions of π-arenes as $G_9$ can be found in EP-A 94 915. Examples of preferred π-arenes as $G_8$ are toluene, xylene, ethylbenzene, cumene, methoxybenzene, methylnaphthalene, pyrene, perylene, stilbene, diphenylene oxide and diphenylene sulfide. Cumene, methylnaphthalene and stilbene are especially preferred.

Preferred as anion T are $PF_6^-$, $AsF_6^-$, $SbF_6^-$, $CF_3SO_3^-$, $C_2F_5SO_3^-$, n-$C_3F_7SO_3^-$, n-$C_4F_9SO_3^-$, n-$C_6F_{13}SO_3^-$ and n-$C_8F_{17}SO_3^-$.

The metallocene salts can also be used in combination with oxidising agents. Such combinations are described in EP-A 126 712.

In order to increase light power it is also possible, in dependence upon the type of initiator, to use sensitisers. Examples thereof are polycyclic aromatic hydrocarbons or aromatic keto compounds. Specific examples of preferred sensitisers are mentioned in EP-A 153 904.

Photoinitiators are added in effective amounts, for example in amounts of from approximately 0.1 to approximately 10% by weight each, based on the total amount of the mixture. When the mixtures according to the invention are used for stereolithographic processes, in which laser beams are usually used, it is essential that the absorption capacity of the mixtures is so matched in terms of the type and the concentration of the photoinitiator that the curing depth at normal laser speed is approximately from 0.1 to 2.5 mm. The total amount of photoinitiators in the compositions according to the invention is preferably from 0.5 to 5% by weight.

The mixtures according to the invention may also comprise various photoinitiators having different photosensitivity to rays of emission lines of different wavelengths. As a result, for example, there is obtained better utilisation of an UV/VIS light source that irradiates emission lines of different wavelengths. In that case it is advantageous for the different photoinitiators to be so selected and to be used in such concentrations that an equal optical absorption is produced for the emission lines used.

It is often advantageous to add further constituents to the compositions according to the invention, for example customary additives, such as stabilisers, for example UV stabilisers, polymerisation inhibitors, parting agents, wetting agents, flow agents, sensitisers, anti-settling agents, surface-active agents, dyes, pigments or fillers. Those additives are each used in an amount effective for the desired purpose and can constitute a total of, for example, up to 20% by weight of the compositions according to the invention.

The compositions may also, if desired, comprise up to 50% by weight of a hydroxy-terminated polyether or polyester, for example di- or tri-functional polyethers or polyester-polyols, polytetrahydrofuran, hydroxy-terminated polyurethanes or, preferred of the mentioned components, poly-ε-caprolactam.

Preferred compositions comprise 5 to 60% by weight of one or more of the vinyl ether compounds according to the invention;

0 to 40% by weight of mono-, di- or poly-functional acrylates or methacrylates;

30 to 80% by weight of di- or poly-functional epoxy compounds;

0 to 5% by weight of radical photoinitiators;

0.5 to 5% by weight of cationic photoinitiators;

0 to 40% by weight of hydroxy-terminated polyethers or polyesters; and 0 to 10% by weight of one or more additives.

The compositions can be prepared in known manner, for example by pre-mixing individual components and subsequently mixing those premixes together or by mixing all the components together using customary apparatus, such as stirred containers, in the absence of light and if desired at slightly elevated temperature.

The compositions according to the invention can be polymerised by irradiation with actinic light, for example by means of electron, X-ray, UV or VIS light, that is to say preferably with rays in a wavelength range of 280–650 nm. Especially suitable are laser beams of HeCd, argon or nitrogen, and also metal vapour and NdYAG lasers. It is known to the person skilled in the art that for each light source selected the suitable photoinitiator must be selected and if necessary sensitised. It has been found that the penetration depth of the rays into the composition to be polymerised and the operating speed are directly connected with the absorption coefficient and the concentration of the photoinitiator. In stereolithography it is preferable to use those photoinitiators which bring about the highest number of resultant free radicals or cationic particles and allow the greatest depth of penetration of the radiation into the compositions to be polymerised.

The invention relates also to a method of producing a cured product in which compositions, as described above, are treated with actinic radiation. For example, the compositions according to the invention can be used as adhesives, as surface-coatings, as photoresists, for example as solder resists, or for rapid prototyping, especially for stereolithography.

The invention therefore relates also to a method of producing three-dimensional objects from the liquid mixtures according to the invention by means of stereolithographic processes, comprising a step in which the surface of a layer of the liquid mixture according to the invention is irradiated over its entire surface or in a predetermined pattern with an UV/VIS light source, so that in the irradiated regions a layer of the desired thickness is solidified, and then a fresh layer of the mixtures according to the invention is formed on the solidified layer, and that fresh layer is likewise irradiated over its entire surface or in a predetermined pattern, and as a result of the repeated coating and irradiation there are obtained three-dimensional objects consisting of a number of solidified layers adhering one to another.

In that method it is preferable to use as the radiation source a laser beam, which is preferably computer-controlled.

In general, the first radiation curing described above, which results in so-called green models which are not yet sufficiently solid, is followed by the final full cure of the mouldings by heating and/or further irradiation.

When used as surface-coatings, the mixtures according to the invention produce clear, hard surface-coatings on wood, paper, metal, ceramics and other surfaces. The thickness of the surface-coating can vary to a very great extent and may be from approximately 1 μm to approximately 1 mm. The mixtures according to the invention can be used to produce relief images for printed circuits or printing plates directly by irradiation of the mixtures, for example by means of a computer-controlled laser beam of suitable wavelength or using a photomask and a corresponding light source.

EXAMPLE 1

Preparation of a vinyl ether compound having the formula:

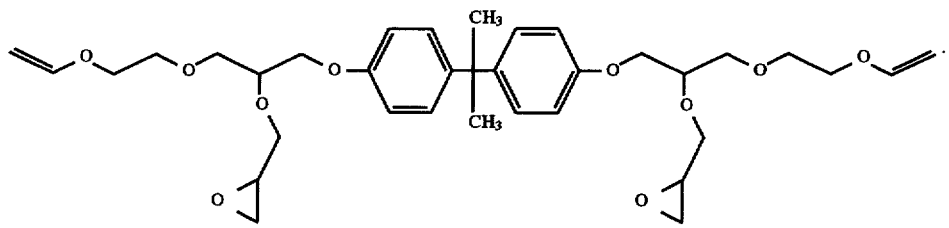

A) 111.7 g (0.3 mol) of the diglycidyl ether of bisphenol A (Araldit® GY 250) are heated at 120° C. with 52.87 g (0.6 mol) of hydroxyethylvinyl ether and 0.1 g of KOH under a nitrogen atmosphere. The mixture is then stirred for 12 hours at that temperature and then for 48 hours at 150° C.

B) 63 g (0.12 mol) of the divinyl ether so obtained are stirred for one hour at 70° C. with 178 g (1.92 mol) of epichlorohydrin and 1.57 g of a 50% tetramethylammonium chloride solution (TMAC). Then, under reduced pressure, 19.2 g of a 50% NaOH solution are added dropwise thereto (90 mbar; 79° C.), the water formed being separated off in a water separator. When the separation of water is complete, the excess epichlorohydrin is distilled off and the residue is taken up in 200 ml of toluene. The resulting NaCl is filtered off and the filtrate is extracted with $NaHCO_3$ solution and water. The organic phase is finally dried and the solvent is removed in a rotary evaporator. 70.8 g (93.8% of the theoretical yield) of the desired product are obtained in the form of a viscous, brownish resin the epoxy content of which is 2.8 equivalents/kg (88.3% of theory).

EXAMPLE 2

Preparation of a vinyl ether compound having the formula:

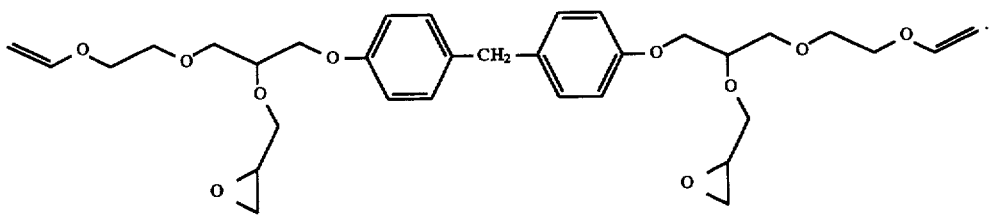

A) 156.2 g (0.5 mol) of the diglycidyl ether of bisphenol F (Araldit® PY 306) are heated at 120° C. with 88.11 g (1.0 mol) of hydroxyethylvinyl ether and 0.17 g of KOH under a nitrogen atmosphere. The mixture is then stirred for 12 hours at that temperature and then for 48 hours at 150° C.

B) 150 g (0.5 mol) of the divinyl ether so obtained are stirred for one hour at 70° C. with 499.54 g (5.4 mol) of epichlorohydrin and 4.5 g of a 50% tetramethylammonium chloride solution. Then, under reduced pressure, 54.4 g of a 50% NaOH solution are added drop-wise thereto and, with separation of water, reaction and working-up are carried out in accordance with Example 1. 148 g (78% of the theoretical yield) of the desired product are obtained in the form of a viscous, yellowish liquid the epoxy content of which is 2.55 equivalents/kg (71.1% of theory).

EXAMPLE 3

Preparation of a vinyl ether compound having the formula:

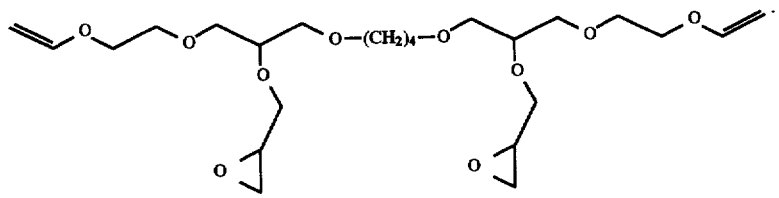

A) 101.13 g (0.5 mol) of the diglycidyl ether of butanediol A (Araldit® DY 026) are heated at 120° C. with 88.11 g (1.0 mol) of hydroxyethylvinyl ether and 0.17 g of KOH under a nitrogen atmosphere. The mixture is then stirred for 12 hours at that temperature and then for 48 hours at 150° C.

B) 150 g (0.39 mol) of the divinyl ether so obtained are stirred for one hour at 70° C. with 569.6 g (5.96 mol) of epichlorohydrin and 5.1 g of a 50% tetramethylammonium chloride solution. Then, under reduced pressure, 59.2 g of a 50% NaOH solution are added dropwise thereto (90 mbar). With separation of water, working-up is carried out in accordance with Example 1. 159.5 g (83.5% of the theoretical yield) of the desired product are obtained in the form of a colourless liquid the epoxy content of which is 3.52 equivalents/kg (86.2% of theory).

EXAMPLE 4

Preparation of a vinyl ether compound having the formula:

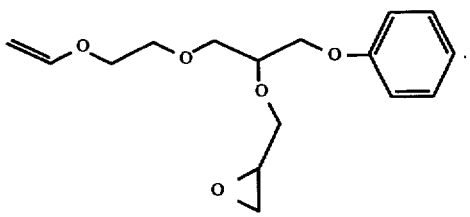

A) 158.08 g (1.0 mol) of phenyl glycidyl ether are reacted with 88.11 g (1.0 mol) of hydroxyethylvinyl ether and 0.34 g of KOH in accordance with Example 1.

B) 100 g (0.42 mol) of the divinyl ether so obtained are reacted with 621.2 g (6.71 mol) of epichlorohydrin and 5.59 g of a 50% tetramethylammonium chloride solution in accordance with Example 1. After the dropwise addition of 67.2 g of a 50% NaOH solution, working-up is carried out, with separation of water, in accordance with Example 1. 116.48 g (94% of the theoretical yield) of the desired product are obtained in the form of a yellowish liquid the epoxy content of which is 3.4 equivalents/kg (87% of theory).

EXAMPLE 5

Preparation of a vinyl ether compound having the formula:

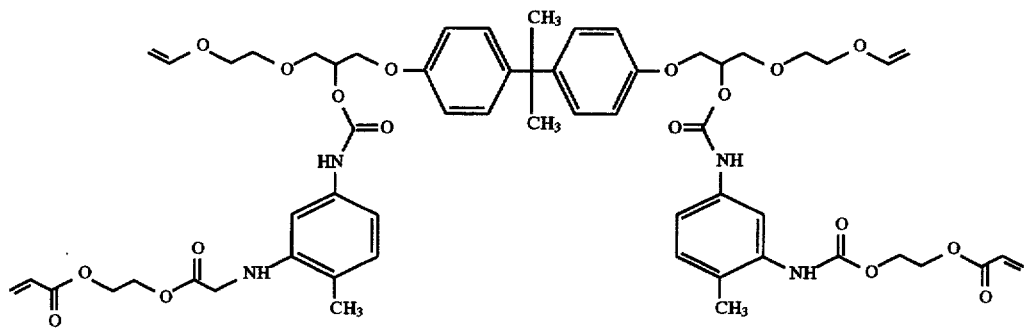

65.89 g (0.38 mol) of toluylene diisocyanate am heated at 35° C., with stirring, with 0.33 g of 2,2'-methylene-bis(6-tert-butyl-4-methylphenol) (Ralox® 46), and 43.93 g (0.38 mol) of hydroxyethyl acrylate are added dropwise thereto. The mixture is stirred for 8 hours at 35° C. until an isocyanate content of 3.4 equivalents/kg is obtained. Then 100 g (0.19 mol) of the divinyl ether from Example 1A), dissolved in 100 ml of toluene, are added dropwise. After 4 hours at 35° C. an isocyanate content of 1.17 equivalents/kg is determined. 0.24 g of dibutyltin laurate is then added and after a further 2 hours at 35° C. the isocyanate content is 0.07 equivalents/kg. The solvent is removed in a rotary evaporator and the residue is dried under a high vacuum. 200 g (95% of the theoretical yield) of the desired product are obtained in the form of a very viscous, yellow resin. GPC indicates a molecular weight of Mn=1430; Mw=6850.

mol) of allyl alcohol are added dropwise thereto. The reaction mixture is cooled in order that an (internal) temperature of 60° C. is not exceeded. After 40 minutes, 50 ml of toluene are added and the isocyanate content of the solution is determined (2.99 equivalents/kg). Then a solution of 50 g (0.097 mol) of the divinyl ether from Example 1A) in 50 ml of toluene is added dropwise and the reaction mixture is stirred for about 24 hours at 45° C. After the addition of 0.12 g of dibutyltin laurate, the mixture is stirred for a further 4 hours at 35° C., the isocyanate content falling to 0.04 equivalents/kg. Removal of the solvent in a rotary evaporator and drying of the residue under a high vacuum yield 87.8 g (92% of the theoretical yield) of the desired product in the form of a very viscous, yellow resin (Mn=1270; Mw=7880; determined with GPC).

EXAMPLE 6

Preparation of a vinyl ether compound having the formula:

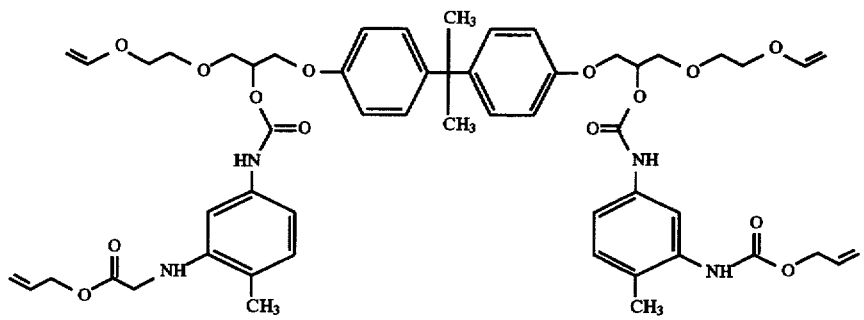

33.7 g (0.19 mol) of toluylene diisocyanate are heated at 35° C., with stirring, with 0.25 g of Ralox® 46, and 11.25 g (0.19

EXAMPLE 7

Preparation of a vinyl ether compound having the formula:

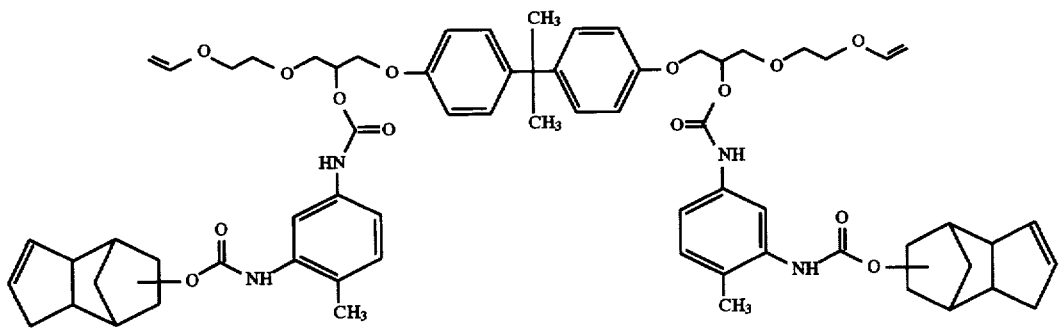

67.42 g (0.387 mol) of toluylene diisocyanate are heated at 35° C., with stirring, with 0.5 g of Ralox® 46, and 58.13 g (0.387 mol) of tricyclodecane alcohol E (HOECHST) are slowly added dropwise thereto. The reaction mixture is cooled in order that an (internal) temperature of 35° C. is not exceeded. After 1.5 hours the isocyanate content of the solution is 3.08 equivalents/kg. The mixture is diluted with 50 ml of toluene. Then a solution of 100 g (0.193 mol) of the divinyl ether from Example 1A) in 100 ml of toluene is added dropwise thereto. After 8 hours at 35° C. the isocyanate content is 0.35 equivalents/kg. After the addition of 0.24 g of dibutyltin laurate the mixture is stirred for a further 4 hours at 35° C., the isocyanate content falling to 0.06 equivalents/kg. Removal of the solvent in a rotary evaporator and drying of the residue under a high vacuum yield 209.5 g (92.9% of the theoretical yield) of the desired product in the form of a viscous, yellow resin (Mn=1220; Mw=5130; determined with GPC).

EXAMPLE 8

Preparation of a vinyl ether compound having the formula:

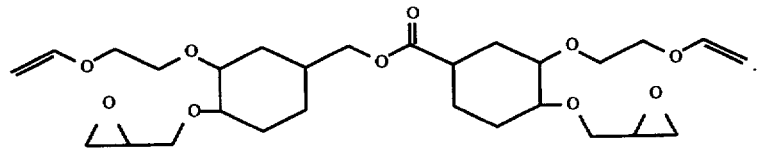

A) 137.3 g (0.5 mol) of 3,4-epoxycyclohexylmethyl-3', 4'-epoxycyclohexanecarboxylate (Araldit® CY 179) are reacted with 88.11 g (1.0 mol) of hydroxyethylvinyl ether and 0.072 g of KOH in accordance with Example 1.

B) 150 g (0.35 mol) of the divinyl ether so obtained are reacted with 518.1 g (5.60 mol) of epichlorohydrin and 4.66 g of a 50% tetramethylammonium chloride solution according to Example 1. After the dropwise addition of 56 g of a 50% NaOH solution, working-up is carried out, with separation of water, in accordance with Example 1. 153.8 g (80.9% of the theoretical yield) of the desired product are obtained in the form of a brownish liquid the epoxy content of which is 2.34 equivalents/kg (63.1% of theory).

EXAMPLE 9

Preparation of a vinyl ether compound having the formula:

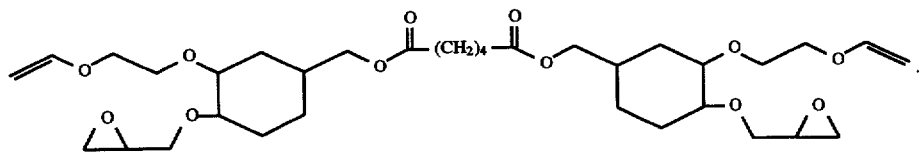

A) 161.1 g (0.4 mol) of a cycloaliphatic epoxy resin of the formula

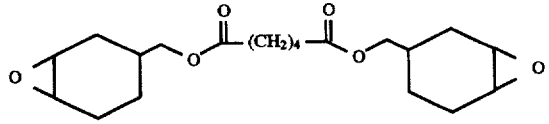

(Araldit® CY 177) are reacted with 70.5 g (0.8 mol) of hydroxyethylvinyl ether and 0.058 g of KOH in accordance with Example 1.

B) 150 g (0.23 mol) of the divinyl ether so obtained are reacted with 340.47 g (3.68 mol) of epichlorohydrin and 3.06 g of a 50% tetramethylammonium chloride solution according to Example 1. After the dropwise addition of 36.8 g of a 50% NaOH solution, working-up is carried out, with separation of water, in accordance with Example 1.113.7 g (75.5% of the theoretical yield) of the desired product are obtained in the form of a brownish liquid the epoxy content of which is 1.04 equivalents/kg (34.1% of theory).

EXAMPLE 10

Preparation of a vinyl ether compound having the formula:

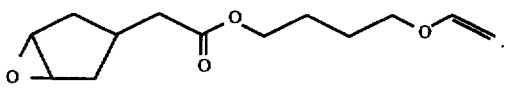

A) 43.46 g (0.31 mol) of cyclopentenylacetic acid methyl ester are dissolved in 80 ml of chloroform. After the addition of 4 g of sodium acetate, 82.51 g of a 40% solution of peracetic acid in acetic acid are added dropwise thereto, with stirring, the temperature being maintained at about 35° C. The reaction mixture is then stirred for a further 5 hours at 35° C. The reaction mixture is extracted with 5% sodium hydrogen carbonate solution and then twice with water. The organic phase is then separated off and dried and residual peroxide is destroyed with sodium sulfite. After distillation of the organic phase there are obtained 32.3 g of 3,4-epoxycyclopentylacetic acid methyl ester (66.5% of theory).

B) In a sulfonating flask equipped with an agitator, thermometer and a distillation attachment having a Vigreux column, 29.87 g (0.19 mol) of that epoxide are heated at reflux, under nitrogen, with 44.43 g (0.38 mol) of hydroxybutylvinyl ether and 0.04 g of titanium tetraisopropyl oxide. The methanol that is formed is continuously distilled off, so that after about 11 hours 6.7 g of methanol have been separated. The excess hydroxybutylvinyl ether is then distilled off under a high vacuum at 80° C. The residue is dissolved in ethyl acetate, extracted with a 5% sodium hydrogen carbonate solution and then with water. After removal of the solvent with the aid of a rotary evaporator there are obtained 42.23 g of the desired epoxyvinyl ether (92.5% of the theoretical yield (GC 98%)).

EXAMPLE 11

Preparation of a vinyl ether compound having the formula:

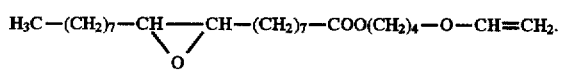

A) In accordance with the instructions of R. F. Storey, T. P. Hickey; J. Polym. Sci. A, Polym. Chem. 31 (1993), p. 1825, first of all 148.24 g (0.5 mol) of oleic acid methyl ester (technical isomeric mixture) are dissolved in 300 ml of chloroform. Then 255 g (0.6 mol) of 8% $H_2O_2$, 4 g (0.01 mol) of tricaprylmethylammonium chloride (Aliquat® 336), 8.2 g (0.025 mol) of sodium tungstate hydrate and 4.9 g (0.05 mol) of phosphoric acid are added. The mixture is stirred for 5 hours at 60° C. Then the organic phase is separated off, extracted with a 5% $NaHCO_3$ solution and water and dried and the residual peroxides are destroyed with sodium sulfite. The solvent is removed in a rotary evaporator and the residue is dried for 2 hours under a high vacuum. 155.7 g of an orange-brown oil having an epoxy content of 3.03 equivalents/kilogram (94.7% of theory) are obtained.

B) In a sulfonating flask equipped with an agitator, thermometer and distillation attachment, 50 g (0.16 mol) of that epoxide are dissolved in 100 ml of toluene, and 37.17 g (0.32 mol) of hydroxybutylvinyl ether and 3.74 g of dibutyltin oxide are added. The mixture is heated at 105° C., with stirring, a mixture of methanol and toluene being distilled off. The reaction is continued until starting material can no longer be detected in GC (about 11 hours). After removal of the excess hydroxybutylvinyl ether, the residue is dissolved in dichloromethane and extracted with $NaHCO_3$ and water as described above. Removal of the solvent in a rotary evaporator and drying of the residue under a high vacuum yield 63 g of the desired product (99.2% of the theoretical yield; GC about 94%).

EXAMPLE 12

Preparation of a vinyl ether compound having the formula:

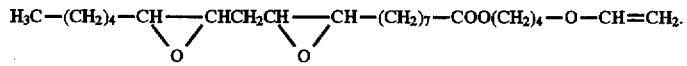

A) Analogously to Example 11A), 143.9 g (0.49 mol) of linoleic acid methyl ester are reacted with 1008.72 g (2.39 mol) of 8% $H_2O_2$ with the addition of 8.86 g of Aliquat® 336, 16.06 g of sodium tungstate and 9.59 g of phosphoric acid. After removal of the solvent there is obtained a yellow oil in a yield of 154.2 g (96.4% of the theoretical yield) having an epoxy content of 4.15 equivalents/kilogram (67.7% of theory).

B) Analogously to Example 10B), 148.76 g (0.456 mol) of that epoxide are reacted with 76.99 g (0.68 mol) of hydroxybutylvinyl ether and 0.21 g of titanium tetraisopropyl oxide. After about 11 hours the separation of methanol has ceased. 179.27 g (95.5% of the theoretical yield) of the desired product are isolated.

EXAMPLE 13

Preparation of a vinyl ether compound having the formula:

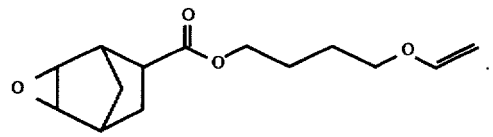

A) Analogously to Example 11A), 120 g (0.788 mol) of 5-carbomethoxy-2-norbornene are reacted with 807.8 g (1.9 mol) of 8% $H_2O_2$ with the addition of 6.37 g of Aliquat® 336, 13.7 g of sodium tungstate and 7.12 g of phosphoric acid. After distillation under reduced pressure there are obtained 56.8 g (42.9% of the theoretical yield) of epoxide.

B) Analogously to Example 10B), 56 g (0.33 mol) of that epoxide are reacted with 77.4 g (0.66 mol) of hydroxybutylvinyl ether and 0.2 g of titanium tetraisopropyl oxide. After removal of the excess hydroxybutylvinyl ether and extraction of the organic phase as described in Example 10B), 92 g of a yellowish liquid are isolated. Distillation of 20 g of that liquid yields 14.9 g of the desired epoxyvinyl ether (boiling point 116°–118° C. at 0.5 mbar pressure).

EXAMPLE 14

Preparation of a vinyl ether compound having the formula:

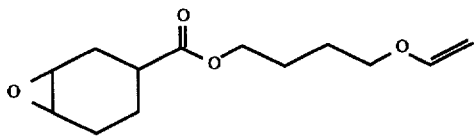

A) Analogously to Example 10 A), 50 g (0.36 mol) of cyclohex-3-enecarboxylic acid methyl ester are reacted with 171.1 g of peracetic acid in acetic acid. After distillation there are obtained 38.9 g (69% of the theoretical yield) of epoxide.

B) Analogously to Example 10 B), 38 g (0.243 mol) of that epoxide are reacted with 56.6 g (0.486 mol) of hydroxybutylvinyl ether and 0.13 g of titanium tetraisopropyl oxide. 92 g (80% of the theoretical yield) of the desired product are isolated in the form of an orange liquid.

EXAMPLE 15

Preparation of a vinyl ether compound having the formula:

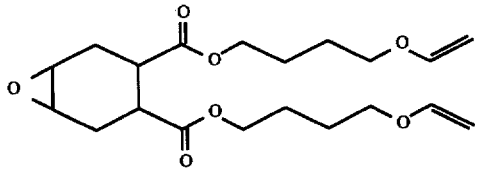

A) Analogously to Example 10 A), 168.80 g (0.85 mol) of tetrahydrophthalic acid dimethyl ester are reacted with 230.1 g of a 40% solution of peracetic acid in acetic acid and 10 g of sodium acetate. 114.2 g (62.7% of the theoretical yield) of epoxide having an epoxy content of 3.39 equivalents/kilogram (72.7% of theory) are obtained.

B) Analogously to Example 11 B), 108.38 g (0.506 mol) of that epoxide are reacted with 232.32 g (2 mol) of hydroxybutylvinyl ether with the addition of 6.81 g of dibutyltin oxide until starting material can no longer be detected in GC (about 11 hours). After removal of the excess hydroxybutylvinyl ether, the residue is extracted with water, yielding 150.12 g of the desired product (98.2% of the theoretical yield).

EXAMPLE 16

The following components are mixed together, with stirring, at 60° C. until a clear solution is formed:

48.4 g of 3,4-epoxycyclohexylmethyl-3',4'-epoxycyclohexanecarboxylate (Araldit® CY 179);

18 g of butanediol diglycidyl ether (Araldit® DY 026);

20 g of the vinyl ether compound from Example 3;

6 g of dipentaerythritol pentaacrylate (Sanomer® 399);

6 g of bisphenol-A-diglycidyl diacrylate (Novacure® 3700);

0.8 g of 1-hydroxycyclohexylphenyl ketone (Irgacure® 184);

0.8 g of a Cyracure® UVI 6974

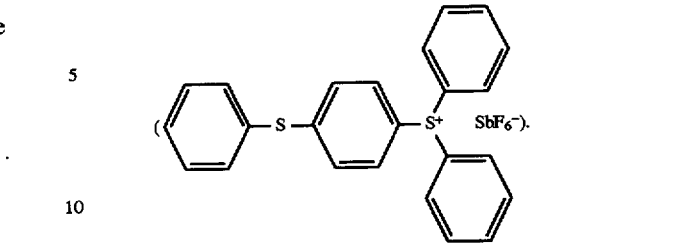

The viscosity of the mixture is 121 mPa.s (30° C.). With the aid of a He/Cd laser, mouldings having dimensions of 45.7×0.38×0.5 mm are produced by irradiation (irradiation energy of 80 mJ/cm$^2$). Immediately after the irradiation those mouldings (the so-called green models) have the following properties:

modulus of elasticity (E modulus) according to ISO R 527=544 MPa;

elongation at tear according to ISO R 527, determined with the Lloyd® 500 testing machine manufactured by Lloyd, =23.3%.

For complete full cure the green models are irradiated for 30 minutes with UV light and then heated for 30 minutes at a temperature of 130° C. The following properties are then measured:

modulus of elasticity=2586 MPa;

elongation at tear=2%;

impact strength according to ISO 179/1 D=8.7 kJ/cm$^2$;

curl factor (mouldings of the "Weave" type according to P. Jacobs, Rapid Prototyping+Manufacturing, Fundamentals of Stereolithography, Soc. of Manufact. Engineers, 1992, p. 256) =−0.12.

EXAMPLE 17

The following components are mixed together, with stirring, at 60° C. until a clear solution is formed:

48.4 g of 3,4-epoxycyclohexylmethyl-3',4'-epoxycyclohexanecarboxylate (Araldit® CY 179);

18 g of the vinyl ether compound from Example 3;

20 g of a trifunctional, hydroxy-terminated polycaprolactone (Tone® 0301);

6 g of dipentaerythritol pentaacrylate (Sartomer® 399);

6 g of bisphenol-A-diglycidyl diacrylate (Novacure® 3700);

0.8 g of 1-hydroxycyclohexylphenyl ketone (Irgacure® 184);

0.8 g of a triarylsulfonium hexafluoroantimonate initiator (Cyracure® UVI 6974).

The viscosity of the mixture is 387 mPa.s (30° C.). With the aid of a He/Cd laser, mouldings having dimensions of 45.7×0.38×0.51 mm are produced by irradiation (irradiation energy of 80 mJ/cm$^2$). Immediately after the irradiation those mouldings (the so-called green models) have the following properties:

modulus of elasticity (E modulus) =90.8 MPa;

elongation at tear=70%.

For complete full cure the green models are irradiated for 30 minutes with UV light and then heated for 30 minutes at a temperature of 130° C. The following properties are then measured:

modulus of elasticity=2663 MPa;

elongation at tear=16.8%;

impact strength according to ISO 179/1D=42 kJ/cm²;
curl factor (mouldings of the "Weave" type) =0.013.

EXAMPLE 18

The following components are mixed together, with stirring, at 60° C. until a clear solution is formed:

48.4 g of 3,4-epoxycyclohexylmethyl-3',4'-epoxycyclohexanecarboxylate (Araldit® CY 179);

18 g of the vinyl ether compound from Example 4;

20 g of a trifunctional, hydroxy-terminated polycaprolactone (Tone® 0301);

6 g of dipentaerythritol pentaacrylate (Sartomer® 399);

6 g of bisphenol-A-diglycidyl diacrylate (Novacure® 3700);

0.8 g of 1-hydroxycyclohexylphenyl ketone (Irgacure® 184);

0.8 g of a triarylsulfonium hexafluoroantimonate initiator (Cyracure® UVI 6974).

The viscosity of the mixture is 281 mPa.s (30° C.). With the aid of a He/Cd laser, mouldings having dimensions of 45.7×0.38×0.51 mm are produced by irradiation (irradiation energy of 160 mJ/cm²). Immediately after the irradiation those mouldings (the so-called green models) have the following properties:

modulus of elasticity (E modulus) =244 MPa;

elongation at tear=86%.

For complete full cure the green models are irradiated for 30 minutes with UV light and then heated for 30 minutes at a temperature of 130° C. The following properties are then measured:

modulus of elasticity=3083 MPa;

elongation at tear=8.1%;

impact strength according to ISO 179/1D=31.9 kJ/cm²;

curl factor (mouldings of the "Weave" type) =0.0017.

EXAMPLE 19

The following components are mixed together, with stirring, at 60° C. until a clear solution is formed:

48.4 g of 3,4-epoxycyclohexylmethyl-3',4'-epoxycyclohexanecarboxylate (Araldit® CY 179);

18 g of the vinyl ether compound from Example 10;

20 g of a trifunctional, hydroxy-terminated polycaprolactone (Tone® 0301);

6 g of dipentaerythritol pentaacrylate (Sartomer® 399);

6 g of bisphenol-A-diglycidyl diacrylate (Novacure® 3700);

0.8 g of 1-hydroxycyclohexylphenyl ketone (Irgacure® 184);

0.8 g of a triarylsulfonium hexafluoroantimonate initiator (Cyracure® UVI 6974).

The viscosity of the mixture is 224 mPa.s (30° C.).

With the aid of a He/Cd laser, mouldings having dimensions of 40×4.25×2.5 mm are produced by irradiation (Weave type). Immediately after the irradiation those mouldings have an E modulus from the flexural test (according to ISO 178/75) of 436 MPa.

For complete full cure the green models are irradiated for 60 minutes with UV light and then heated for 30 minutes at a temperature of 100° C. The following properties are then measured:

modulus of elasticity (according to ISO R 527) =2718 MPa;

tensile strength (according to ISO R 527)=63 MPa;

elongation at tear=7.3%;

impact strength (according to DIN 52453)=22.5 kJ/cm².

EXAMPLE 20

48.4 g of 3,4-epoxycyclohexylmethyl-3',4'-epoxycyclohexanecarboxylate (Araldit® CY 179);

7 g of the vinyl ether compound from Example 15;

20 g of a glycidylised castor oil (Heloxy® 505);

18 g of a polyester-polyol (Desmophen® 850);

5 g of dipentaerythritol pentaacrylate (Sartomer® 399);

0.8 g of Irgacure® 184;

0.8 g of a triarylsulfonium hexafluoroantimonate initiator (Cyracure® UVI 6974).

The viscosity of the mixture is 600 mPa.s (30° C.).

After laser curing the material has a modulus of elasticity (E modulus) of 201 MPa.

For complete full cure the material is likewise irradiated for 60 minutes with UV light and heated for 30 minutes at a temperature of 100° C. The following properties are then measured:

modulus of elasticity=2043 MPa;

tensile strength=47.7 MPa;

elongation at tear=16%;

impact strength=37 kJ/m².

The cud factor of a test specimen of Weave-type construction was 0%.

EXAMPLE 21

The following components are mixed together, with stirring, at 60° C.:

48.4 g of 3,4-epoxycyclohexylmethyl-3',4'-epoxycyclohexanecarboxylate (Araldit® CY 179);

12 g of the vinyl ether compound from Example 15;

20 g of a glycidylised castor oil (Heloxy® 505);

13 g of a polyester-polyol (Desmophen® 850);

5 g of a trifunctional, hydroxy-terminated polycaprolactone (Tone® 0301);

1.6 g of a triarylsulfonium hexafluoroantimonate initiator (Cyracure® UVI 6974).

The viscosity of the mixture is 400 mPa.s (30° C.).

After laser curing the material has a modulus of elasticity (E modulus) of 348.4 MPa.

For complete full cure the material is likewise irradiated for 60 minutes with UV light and heated for 30 minutes at a temperature of 100° C. The following properties are then measured:

modulus of elasticity=719 MPa;

tensile strength=28.8 MPa;

elongation at tear=55.7%.

The cud factor of a test specimen of Weave-type construction was −4%.

EXAMPLE 22

The following components are mixed together, with stirring, at 60° C.:

48 g of 3,4-epoxycyclohexylmethyl-3',4'-epoxycyclohexanecarboxylate (Araldit® CY 179);

18 g of the vinyl ether compound from Example 3;

6 g of bisphenol-A-diglycidyl diacrylate (Novacure® 3700);

6 g of dipentaerythritol pentaacrylate (Sartomer® 399);

20 g of a trifunctional, hydroxy-terminated polycaprolactone (Tone® 0301);

1.6 g of diphenyliodonium hexafluoroarsenate;

0.8 g of Irgacure® 184.

The viscosity of the mixture is 450 mPa.s (39° C.).

With the aid of a He/Cd laser, mouldings having dimensions of 40×4.3×3.8 mm are produced by irradiation. Immediately after the irradiation those mouldings have an E modulus from the flexural test (ISO 178/75) of 144.9 MPa.

For complete full cure the green models are irradiated for 60 minutes with UV light and then heated for 30 minutes at 100° C. The following properties are then measured:

E modulus=2811 MPa;

tensile strength=62.1 MPa;

elongation at tear=7.5%.

What is claimed is:

1. A method of producing three-dimensional objects from a composition comprising a compound of the formula $$[H_2C=CH-O]_z-A,$$

the symbols used in that formula and in the formulae below having the following definitions:

A is a z-valent radical selected from the radicals of the following formulae (1), (2), (3) and (4)

$$-[(C_xH_{2x})-O-CH_2-CH(OR^2)-CH_2-O]_t-R^1 \quad (1)$$

$$[-(R^2O)-\text{(ring)}] \quad (2)$$

$$-(C_xH_{2x})-O-\overset{O}{\underset{\|}{C}}-[D]-[\overset{O}{\underset{\|}{C}}-O-(C_xH_{2x})]_{t-1}-\{CH_3\}_{2-t} \quad (3)$$

$$\begin{array}{c} -(C_xH_{2x})-O-\overset{O}{\underset{\|}{C}}-(C_xH_{2x}) \\ [-(C_xH_{2x})-O-\overset{O}{\underset{\|}{C}}-(C_xH_2)]_{k-1} \end{array} \begin{array}{c} R^{14} \\ [E] \\ R^{15} \end{array} O; \quad (4)$$

[D] is a group of the formula $$-(C_xH_{2x})-CH\overset{O}{\diagup}CH-[(C_wH_{2w})-CH\overset{O}{\diagup}CH]_v-(C_yH_{2y})-; \quad (5)$$

[E] is a $C_1$- or a $C_2$-alkylene group;

$R^0$ is a hydrogen atom or a methyl group;

$R^1$ is a z-valent radical selected from aliphatic, cycloaliphatic, aromatic, aliphatic-aromatic and aliphatic-cycloaliphatic hydrocarbon radicals and polyoxyalkylene radicals;

$R^2$ is a radical selected from the radicals of the formulae $$-CH_2-CR^0\overset{O}{\diagup}CH_2 \text{ and } -\overset{O}{\underset{\|}{C}}-NH-R^4-NH-\overset{O}{\underset{\|}{C}}-OR^5;$$

$R^4$ is a group selected from the groups of the formulae (tolyl), (diphenylmethane), (isophorone-type cyclohexane) and $-(C_yH_{2y})-$;

$R^5$ is a group selected from the groups of the formulae $$-(C_mH_{2m})-O-\overset{O}{\underset{\|}{C}}-CH=CH_2,$$

$$-(C_mH_{2m})-O-\overset{O}{\underset{\|}{C}}-\overset{CH_3}{\underset{|}{C}}=CH_2, \ -(C_mH_{2m})-CH=CH_2,$$

$$-(C_mH_{2m})-O-CH_2-CR^0\overset{O}{\diagup}CH_2,$$

$$-(C_mH_{2m})-CR^0\overset{O}{\diagup}CH-(C_iH_{2i+1}),$$

(dicyclopentadienyl groups), (cyclohexenyl-CH_2 and norbornenyl-CH_2 and epoxycyclohexyl-CH_2), $$-\text{(phenyl)}-CR^0\overset{O}{\diagup}CH_2 \text{ and } -\text{(phenyl)}-\overset{CR^0}{\underset{\|}{C}}_{CH_2};$$

$R^6$ is a (2.z)-valent organic group which, together with the carbon atoms $C^\alpha$ and $C^\beta$ of each of the z groups of the formula $$-[(C_xH_{2x})-O-C^\alpha H-C^\beta H(OR^2)]- \quad (6)$$

in a radical of formula (2), forms a cycloaliphatic ring having at least 5 carbon atoms;

$R^{14}$ and $R^{15}$ are each a hydrogen atom or, when [E] is a $C_2$ alkylene group, are each a hydrogen atom or together form a methylene group;

i is an integer from 0 to 20;

m is an integer from 1 to 20;
s is an integer from 2 to 10;
t is an integer from 0 to 10;
u in the individual units of the formula

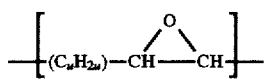

in formula (5) are independently of one another an integer from 1 to 20;
v is an integer from 0 to 4;
x and
y are independently of one another an integer from 2 to 20, and
z is the number 1 or 2,
a photoinitiator and, optionally, at least one other polymerizable compound different from the vinylether compound of formula [$H_2C=CH-O$]—$_z$A, which method comprises a step in which the surface of a layer of the composition is irradiated over its entire surface or in a predetermined pattern with an UV/VIS light source, so that in the irradiated regions a layer of the desired thickness is solidified, and then a fresh layer of the composition is formed on the solidified layer, and that fresh layer is likewise irradiated over its entire surface or in a predetermined pattern, and as a result of the repeated coating and irradiation there are obtained three-dimensional objects consisting of a number of solidified layers adhering one to another.

2. A method according to claim 1 including the polymerisable component having the formula

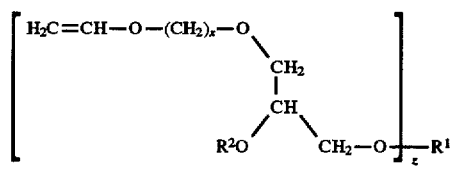

or

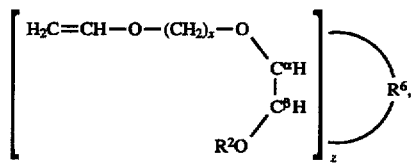

wherein $R^1$, $R^2$, $R^6$, x and z are as defined in claim 1.

3. A method according to claim 1 wherein
$R^1$ is a z-valent radical selected from
a) aliphatic radicals having from 2 to 20 carbon atoms,
b) cycloaliphatic and aromatic radicals each having from 6 to 14 carbon atoms,
c) aliphatic-aromatic and aliphatic-cycloaliphatic radicals each having from 7 to 25 carbon atoms, and
d) polyoxyalkylene radicals of the formulae $R^7$—[$OC_gH_{2g}$]$_n$— and —($C_gH_{2g}$)—[$OC_gH_{2g}$]$_{n-1}$— wherein
$R^7$ is an alkyl group having from 1 to 8 carbon atoms,
g is a number from 1 to 8 corresponding to the average number of carbon atoms of an alkylene unit of the polyoxyalkylene radical and
n is an integer from 2 to 20,
and the radical $R^1$ is unsubstituted or in addition may have one or more substituents which in the case of an aliphatic radical $R^1$ are selected from $C_1$–$C_4$ alkoxy and halogen substituents; and in the case of other types of radical $R^1$ are selected from $C_1$–$C_4$ alkyl, $C_1$–$C_4$ alkoxy and halogen substituents.

4. A method according to claim 3 wherein
$R^1$ is a radical selected from the radicals of the formulae

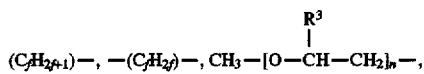

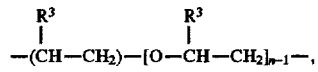

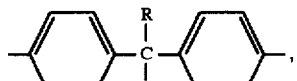

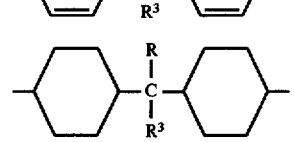

R and
$R^3$ are independently of one another a hydrogen atom or methyl and
f is an integer from 2 to 20.

5. A method according to claim 4 wherein
$R^1$ is a radical selected from the radicals of the formulae

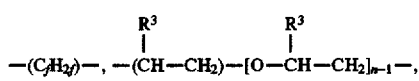

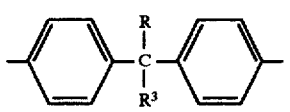

and phenyl;
$R^4$ is a group selected from the groups of the formulae

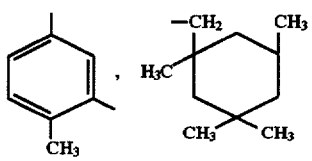

$R^5$ is a group selected from the groups of the formulae

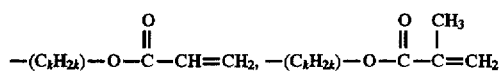

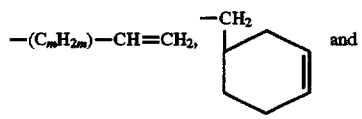

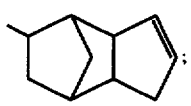

and
R and
$R^3$ are both either a hydrogen atom or methyl; and
k is an integer from 2 to 10, and the index
m has an upper limit of 10.

6. A method according to claim 5 wherein $R^1$ is a radical selected from an alkylene radical having from 2 to 4 carbon atoms, a phenyl radical and a radical of the formula

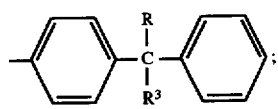

$R^4$ is a group of the formula

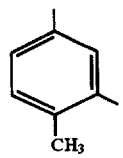

and $R^5$ is a group selected from the groups of the formulae

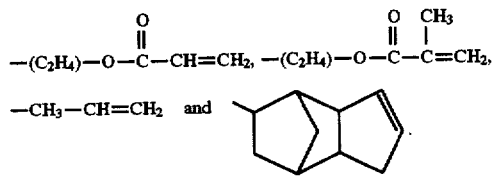

7. A method according to claim 1 wherein
$R^6$ is an organic group having from 3 to 50 carbon atoms.
8. A method according to claim 7 wherein
z is 1 and
$R^6$ together with the carbon atoms $C^\alpha$ and $C^\beta$ of the group of formula (6) forms a cycloalkyl radical having from 5 to 7 ring carbon atoms to which a further cycloalkyl radical having from 5 to 7 ring carbon atoms may have been fused.
9. A method according to claim 8 wherein
$R^6$ together with the carbon atoms $C^\alpha$ and $C^\beta$ of the group of formula (6) forms a cyclopentyl or cyclohexyl radical.
10. A method according to claim 7 wherein
$R^6$ is a group of the formula $R^8$—[G]—$R^9$ wherein
$R^8$ together with the carbon atoms $C^\alpha$ and $C^\beta$ of a group of formula (6) forms a cycloalkyl radical having from 5 to 7 ring carbon atoms to which a further cycloalkyl radical having from 5 to 7 ring carbon atoms may have been fused;
$R^9$ either likewise forms, together with the carbon atoms $C^\alpha$ and $C^\beta$ of a further group of formula (6), a cycloalkyl radical having from 5 to 7 ring carbon atoms to which a further cycloalkyl radical having from 5 to 7 ring carbon atoms may have been fused, or is a cycloalkyl radical having from 5 to 7 ring carbon atoms to which a further cycloalkyl radical having from 5 to 7 ring carbon atoms may have been fused;
[G] is a structural unit selected from a single bond and the groups of the formulae

—O—, —CH$_2$—, —C(CH$_3$)$_2$—, —C(=O)—O—CH$_2$—,

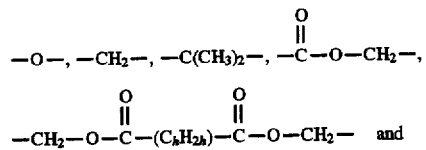

-continued

and h is an integer from 1 to 6, especially from 2 to 4.
11. A method according to claim 10 having the formula

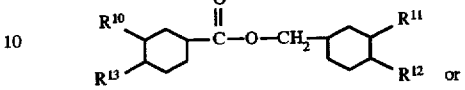

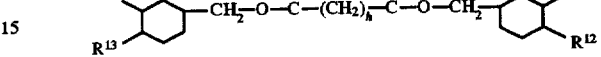

wherein one of the radicals $R^{10}$ and $R^{13}$ is a group of the formula H$_2$C=CH—O—(CH$_2$)$_x$—O— and the other is a group of the formula $R^2$O— and, likewise, one of the radicals $R^{11}$ and $R^{12}$ is a group of the formula H$_2$C=CH—O—(CH$_2$)$_x$—O— and the other is a group of the formula $R^2$O—, and x and h are each independently of the other an integer from 2 to 4.
12. A method according to claim 1 wherein

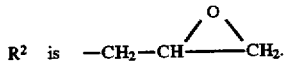

13. A method according to claim 1 wherein
A is a radical of formula (3) or (4), and
s is an integer from 2 to 4,
t is an integer from 0 to 2,
u is the number 1,
v is the number 0 or 1, and
x and
are each an integer from 2 to 10.
14. A method according to claim 1 wherein
A is a radical of formula (4),
$R^{14}$ and
$R^{15}$ are each a hydrogen atom and
z is the number 1.
15. A method according to claim 1 wherein the composition for producing the three-dimensional objects comprises at least one other polymerizable compound different from the vinylether compound of formula [H$_2$C=CH—O]$_z$A.
16. A method according to claim 15 wherein the polymerisable component has the formula

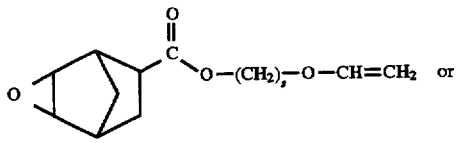

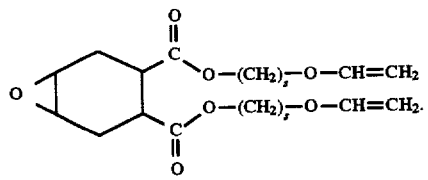

* * * * *